(12) United States Patent
Flohr

(10) Patent No.: US 9,586,970 B2
(45) Date of Patent: Mar. 7, 2017

(54) IMIDAZOLE DERIVATIVES

(71) Applicant: Hoffmann-La Roche Inc., Little Falls, NJ (US)

(72) Inventor: Alexander Flohr, Loerrach (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/162,919

(22) Filed: May 24, 2016

(65) Prior Publication Data

US 2016/0264585 A1  Sep. 15, 2016

Related U.S. Application Data

(63) Continuation of application No. PCT/EP2014/075469, filed on Nov. 25, 2014.

(51) Int. Cl.
*C07D 487/04* (2006.01)
*C07D 403/14* (2006.01)

(52) U.S. Cl.
CPC ......... *C07D 487/04* (2013.01); *C07D 403/14* (2013.01)

(58) Field of Classification Search
CPC ..................... C07D 487/04; C07D 403/14
USPC ............................................... 514/249
See application file for complete search history.

(56) References Cited

U.S. PATENT DOCUMENTS 8,501,795 B2 *  8/2013  Puschl ............... C07D 471/04
                                              514/383

\* cited by examiner

*Primary Examiner* — Yong Chu

(57) ABSTRACT

The present invention relates to compounds of formula (I), wherein A, B, $R^1$ and $R^2$ are

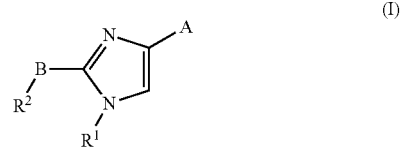

(I)

as defined herein before useful for the treatment of psychiatric disorders.

14 Claims, No Drawings

IMIDAZOLE DERIVATIVES

CROSS REFERENCE TO RELATED APPLICATIONS

This application is a continuation of International Application No. PCT/EP2014/075469 having an international filing date of Nov. 25, 2014 and which claims benefit under 35 U.S.C. §119 to European Patent Application No. 13194931.5 filed Nov. 28, 2013. The entire contents of both are incorporated herein by reference.

FIELD OF THE INVENTION

The present invention relates to novel compounds of formula I, wherein $R^1$, $R^2$, A, and B are as described herein, having pharmaceutical activity, their manufacture, pharmaceutical compositions containing them and their potential use as medicaments.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron* 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets,* 5(4): 507-518, 2001; Nakazato A and Okuyama S, et al., *Exp. Opin. Ther. Patents,* 10(1): 75-98, 2000). This pharmacological approach, besides ameliorating positive symptoms in schizophrenic patients, poorly addresses negative and cognitive symptoms which are the best predictors of functional outcome (Sharma T., *Br. J. Psychiatry,* 174(suppl. 28): 44-51, 1999). In addition, current antipsychotic treatment is associated with adverse effects like weight gain, extrapyramidal symptoms or effects on glucose and lipid metabolism, related to their unspecific pharmacology.

There remains a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D. C. et al., *Biol. Psychiatry,* 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., Physiol. Rev. 1995, 75, 725-748; Conti, M., Jin, S. L., Prog. Nucleic Acid Res. Mol. Biol. 1999, 63, 1-38; Soderling, S. H., Beavo, J. A., Curr. Opin. Cell Biol. 2000, 12, 174-179, Manallack, D. T. et al. J. Med. Chem. 2005, 48 (10), 3449-3462).

The PDE families differ in their substrate specificity for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., Eur. J. Biochem (1999) 266(3):1118-1127, Soderling S. H., et al., Proc. Natl. Acad. Sci. USA (1999) 96(12):7071-7076, Loughney K., et al., Gene (1999) 234(1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distributions of any in the PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., J. Biol. Chem. 1999, 274, 18438-18445, Sweet, L. (2005) WO 2005/012485). On the other hand expression of PDE10A protein has been observed only in enteric ganglia, in testis and epididymal sperm (Coskran T. M., et al., J. Histochem. Cytochem. 2006, 54 (11), 1205-1213).

In the striatum both mRNA and protein are expressed only in the GABA (γ-aminobutyric acid)-containing medium spiny projection neurons making it an intriguing target for the treatment of diseases of the central nervous system (Fujishige, K. et al., Eur. J. Biochem. 1999, 266, 1118-1127; Seeger, T. F. et al., Brain Res. 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. Curr. Biol. 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition. Inhibition of this enzyme pharmacologically or through gene disruption causes a reduction in activity and a reduced response to psychomotor stimulants. Inhibition also reduces the conditioned avoidance response, a behavioral response that is predictive of clinical antipsychotic activity (Siuciak, J. A., et al., Neuropharmacology 2006, 51 (2), 386-396; Siuciak, J. A., et al., Neuropharmacology 2006, 51 (2), 374-385).

In addition, PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J. S., et al., Eur. J. Neuroscience 2005, 2: 1070-1076). In addition increased social interaction in PDE10A2-deficient mice have been observed (Sano, H. J. Neurochem. 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the present invention are also suitable for the treatment of diabetes and related disorders such as obesity by regulating the cAMP signaling system.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

BRIEF SUMMARY OF THE INVENTION

The present invention relates to compounds of formula (I)

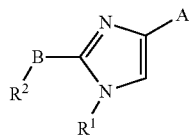

wherein
A is selected from the group consisting of:

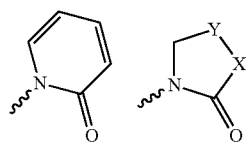

B is $C_1$-$C_4$ alkylene, $C_2$-$C_4$ alkenylene, $C_2$-$C_4$ alkynylene, $R^1$ is selected from hydrogen, $C_1$-$C_7$-alkyl, $C_1$-$C_7$-alkoxyalkyl, $C_1$-$C_7$-haloalkyl, —$(CH_2)_{0,1,2}$—$C_3$-$C_5$-cycloalkyl, —$(CH_2)_{0,1,2}$-(hetero-)aryl optionally substituted by halogen, $C_1$-$C_7$-alkyl or $C_1$-$C_7$ alkoxy, $R^2$ is selected from heteroaryl optionally substituted by 1 to 3 substituents selected from halogen, hydroxyl, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—$R^6$—C(O)—$R^7$, heteroaryl, heterocycloalkyl, —$SO_2R^{12}$—C(O)NR'R", NR'R" wherein R' and R" are independently selected from hydrogen, $C_1$-$C_7$-alkyl or R' and R" together with the nitrogen atom to which they are attached from a heterocycloalkyl or $R^2$ is selected from $C_1$-$C_2$-alkoxy optionally substituted by halogen, $R^6$ and $R^{12}$ are independently selected from $C_1$-$C_7$-alkyl, $R^7$ is selected from heterocycloalkyl, X is $NR^3$ or $CR^3$, Y is $(CH_2)_n$, n is 1, 2, 3, 4, $R^3$ is selected from hydrogen, $C_1$-$C_7$-alkyl.

Further, the invention is concerned with a process for the manufacture of the above compounds, pharmaceutical preparations which contain such compounds and methods for the treatment of neuropsychiatric disorder with these compounds.

DETAILED DESCRIPTION OF THE INVENTION

Definitions

Unless otherwise indicated, the following definitions are set forth to illustrate and define the meaning and scope of the various terms used to describe the invention herein.

The terms "compound(s) of the formula (I)", "compound(s) of formula (I)", "compound(s) of this invention" or "compound(s) of the present invention" refer to any compound selected from the genus of compounds as defined by the formula (I) including stereoisomers, tautomers, solvates, and salts (e.g. pharmaceutically acceptable salts) thereof.

It must be noted that, as used in the specification and the claims, the singular forms "a", "an" and "the" include plural referents unless the context clearly dictates otherwise.

When indicating the number of substituents, the term "one or more" means from one substituent to the highest possible number of substitution, i.e. replacement of one hydrogen up to replacement of all hydrogens by substituents.

The term "optional" or "optionally" denotes that a subsequently described event or circumstance may but need not occur, and that the description includes instances where the event or circumstance occurs and instances in which it does not.

The term "substituent" denotes an atom or a group of atoms replacing a hydrogen atom on the parent molecule.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl, iso-butenyl, and tert-butenyl.

The term "alkenylene" denotes a linear divalent hydrocarbon chain of 2 to 7 carbon atoms or a branched divalent hydrocarbon chain of 3 to 7 carbon atoms with at least one double bond. Exemplary alkenylene include ethenylene, 2,2-dimethylethenylene, propenylene, 2-methylpropenylene, butenylene, and pentenylene.

The term "alkoxy" denotes a group of the formula —O—R', wherein R' is an alkyl group. Examples of alkoxy moieties include methoxy, ethoxy, isopropoxy, and tert-butoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "alkylene" denotes a linear saturated divalent hydrocarbon group of 1 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, hexylene.

The term "alkynylene" denotes a linear divalent hydrocarbon chain of 2-6 carbon atoms or a branched divalent hydrocarbon chain of 3-6 carbon atoms with at least one triple bond. Exemplary alkynylene include ethynylene, 2,2-dimethylethynylene, propynylene, 2-methylpropynylene, butynylene, and pentynylene.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cyanoalkyl" denotes an alkyl group wherein at least one of the hydrogen atoms of the alkyl group has been replaced by a cyano group. Examples of cyanoalkyl include cyanomethyl, cyanoethyl, cyanopropyl, cyano-isopropyl, cyano-isobutyl, cyano-sec-butyl, cyano-tert-butyl, cyano-pentyl or cyanohexyl.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoro-methyl. The term "perhaloalkyl" denotes an alkyl group where all hydrogen atoms of the alkyl group have been replaced by the same or different halogen atoms.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "buffer" denotes a pharmaceutically acceptable excipient, which stabilizes the pH of a pharmaceutical preparation. Suitable buffers are well known in the art and can be found in the literature. Particular pharmaceutically acceptable buffers comprise histidine-buffers, arginine-buffers, citrate-buffers, succinate-buffers, acetate-buffers and phosphate-buffers. Independently from the buffer used, the pH can be adjusted with an acid or a base known in the art, e.g. hydrochloric acid, acetic acid, phosphoric acid, sulfuric acid and citric acid, sodium hydroxide and potassium hydroxide.

The definitions described herein apply irrespective of whether the terms in question appear alone or in combination. It is contemplated that the definitions described herein may be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

The present invention relates to compounds of formula (I)

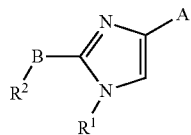

(I)

wherein
A is selected from the group consisting of:

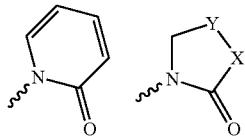

B is $C_1$-$C_4$-alkylene, $C_2$-$C_4$-alkenylene, $C_2$-$C_4$-alkynylene, $R^1$ is selected from hydrogen, $C_1$-$C_7$-alkyl, $C_1$-$C_7$-alkoxyalkyl, $C_1$-$C_7$-haloalkyl, —$(CH_2)_{0,1,2}$—$C_3$-$C_5$-cycloalkyl, —$(CH_2)_{0,1,2}$-(hetero-)aryl optionally substituted by halogen, $C_1$-$C_7$-alkyl or $C_1$-$C_7$ alkoxy, $R^2$ is selected from heteroaryl optionally substituted by 1 to 3 substituents selected from halogen, hydroxyl, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—$R^6$—C(O)—$R^7$, heteroaryl, heterocycloalkyl, —$SO_2R^{12}$—C(O)NR'R", NR'R" wherein R' and R" are independently selected from hydrogen, $C_1$-$C_7$-alkyl or R' and R" together with the nitrogen atom to which they are attached from a heterocycloalkyl or $R^2$ is selected from $C_1$-$C_2$-alkoxy optionally substituted by halogen, $R^6$ and $R^{12}$ are independently selected from $C_1$-$C_7$-alkyl,
$R^7$ is selected from heterocycloalkyl,
X is $NR^3$ or $CR^3$, Y is $(CH_2)_n$,
n is 1, 2, 3, 4,
$R^3$ is selected from hydrogen, $C_1$-$C_7$-alkyl.

In a particular embodiment the present invention relates to compounds of formula (I), wherein $R^2$ is selected from heteroaryl optionally substituted by 1 to 3 substituents selected from halogen, $C_1$-$C_7$-alkyl, $C_1$-$C_7$-haloalkyl, $C_1$-$C_2$-alkoxy optionally substituted by halogen, $C_3$-$C_5$-cycloalkyl, cyano;

In a particular embodiment the present invention relates to compounds of formula (I), wherein A is

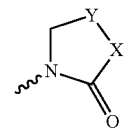

In a particular embodiment the present invention relates to compounds of formula (I), wherein A is

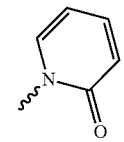

In a particular embodiment the present invention relates to compounds of formula (I), wherein $R^2$ is selected from the group consisting of:

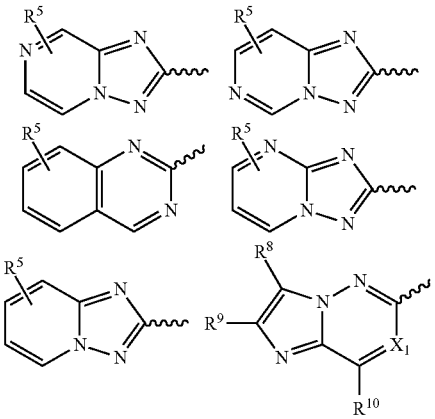

wherein one or more $R^5$ is selected from hydrogen, halogen, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—$R^6$—C(O)—$R^7$, —$SO_2R^8$, $C_1$-$C_2$-alkoxy optionally substituted by halogen, $C_1$-$C_2$-alkoxy or heterocycloalkyl, $R^6$ and $R^8$ are independently selected from $C_1$-$C_7$-alkyl,
$R^7$ is selected from heterocycloalkyl.

$R^8$ and $R^9$ are independently selected from hydrogen, halogen, $C_1$-$C_7$-alkyl, $C_1$-$C_7$-haloalkyl, $C_1$-$C_7$-hydroxyalkyl, cyano, or $R^8$ and $R^9$ together form a $C_3$-$C_8$ cycloalkyl;

$R^{10}$ is selected from hydrogen, $C_1$-$C_7$-haloalkoxy, $C_3$-$C_8$ cycloalkyl, $C_1$-$C_7$ alkoxy, hydroxyl, halogen, $S(O)_2$—$C_1$-$C_7$-alkyl, —C(O)NR'R", NR'R" wherein R' and R" are independently selected from hydrogen, $C_1$-$C_7$-alkyl or R' and R" together with the nitrogen atom to which they are attached from a heterocycloalkyl or $R^{10}$ and $R^4$ together form a $C_3$-$C_8$ cycloalkyl, $R^{11}$ is selected from heteroaryl or heterocycloalkyl, preferably a 5- or 6-membered heteroaryl or a 5- or 6-membered heterocycloalkyl, $X_1$ is N or C—$R^4$ wherein $R^4$ is selected from hydrogen, $C_1$-$C_7$-alkyl, $C_1$-$C_7$ alkoxy, $C_1$-$C_7$-haloalkyl, $C_3$-$C_8$ cycloalkyl, —C(O)NR'R" wherein R' and R" are independently selected from hydrogen and $C_1$-$C_7$-alkyl.

In a particular embodiment the present invention relates to compounds of formula (I), wherein $R^2$ is selected from the group consisting of:

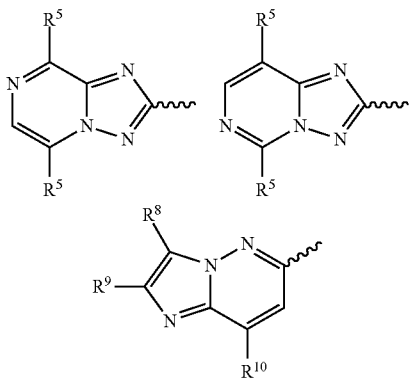

wherein $R^5$ is independently selected from hydrogen, halogen, $C_{1-7}$ alkyl, $C_1$-$C_7$-haloalkyl, $R^8$ and $R^9$ are independently selected from $C_{1-7}$ alkyl, $C_1$-$C_7$-haloalkyl and $R^{10}$ is selected from hydrogen and —C(O)NR'R", wherein R' and R" are independently selected from hydrogen and $C_1$-$C_7$-alkyl.

In a particular embodiment the present invention relates to compounds of formula (I), wherein B is selected from ethylene, ethenylene and ethynylene.

In a particular embodiment the present invention relates to compounds of formula (I), wherein X is $CR^3$ and Y is $CH_2$, wherein $R^3$ is hydrogen.

In a particular embodiment the present invention relates to compounds of formula (I), wherein X is $NR^3$ and Y is $CH_2$, wherein $R^3$ is $C_{1-7}$ alkyl.

In a particular embodiment the present invention relates to compounds of formula (I), wherein $R^1$ is selected from $C_1$-$C_7$-alkyl, $C_1$-$C_7$-haloalkyl, —$(CH_2)_{0,1,2}$—$C_3$-$C_5$-cycloalkyl, phenyl.

In a particular embodiment the present invention relates to compounds of formula (I) selected from the group consisting of:

1-(2-(2-(5,8-dimethyl-[1,2,4]triazolo[1,5-c]pyrimidin-2-yl) ethyl)-1-methyl-1H-imidazol-4-yl)pyrrolidin-2-one
1-(2-(2-(5,8-dimethyl-[1,2,4]triazolo[1,5-a]pyrazin-2-yl) ethyl)-1-phenyl-1H-imidazol-4-yl)pyrrolidin-2-one
1-[2-[(E)-2-(5,8-dimethyl-[1,2,4]triazolo[1,5-a]pyrazin-2-yl) ethenyl]-1-phenylimidazol-4-yl]pyrrolidin-2-one
1-(1-(Cyclopropylmethyl)-2-(2-(5, 8-dimethyl-[1,2,4]triazolo[1,5-a]pyrazin-2-yl)ethyl)-1H-imidazol-4-yl)pyridin-2(1H)-one
1-(2-(2-(5,8-dimethyl-[1,2,4]triazolo[1,5-a]pyrazin-2-yl) ethyl)-1-methyl-1H-imidazol-4-yl)pyridin-2(1H)-one
1-[1-cyclopropyl-2-[(E)-2-(5,8-dimethyl-[1,2,4]triazolo[1, 5-a]pyrazin-2-yl)ethenyl]imidazol-4-yl]pyrrolidin-2-one
1-(1-cyclopropyl-2-(2-(5, 8-dimethyl-[1,2,4]triazolo[1,5-a] pyrazin-2-yl)ethyl)-1H-imidazol-4-yl)pyrrolidin-2-one
1-[2-[(E)-2-(5,8-dimethyl-[1,2,4]triazolo[1,5-a]pyrazin-2-yl)vinyl]-1-methyl-imidazol-4-yl]-3-methyl-imidazolidin-2-one
1-(2-((4, 8-dimethylquinazolin-2-yl)ethynyl)-1-methyl-1H-imidazol-4-yl)pyrrolidin-2-one
1-{2-[(E)-2-{4,7-dimethyl-[1,2,4]triazolo[1,5-a]pyrazin-2-yl}ethenyl]-1-methyl-1H-imidazol-4-yl}pyrrolidin-2-one
1-[2-(2-{4,7-Dimethyl-[1,2,4]triazolo[1,5-a]pyrazin-2-yl}ethyl)-1-methyl-1H-imidazol-4-yl]pyrrolidin-2-one
1-(1-(Cyclopropylmethyl)-2-(2-{4,7-dimethyl-[1,2,4]triazolo[1,5-a]pyrazin-2-yl}ethyl)-1H-imidazol-4-yl]pyrrolidin-2-one
1-[2-(2-{4,7-Dimethyl-[1,2,4]triazolo[1,5-a]pyrazin-2-yl}ethyl)-1-(2,2,2-trifluoroethyl)-1H-imidazol-4-yl]pyrrolidin-2-one
1-[1-(2,2-difluoroethyl)-2-(2-{4,7-dimethyl-[1,2,4]triazolo[1,5-a]pyrazin-2-yl}ethyl)-1H-imidazol-4-yl]pyrrolidin-2-one
1-[2-(2-{4,7-Dimethyl-[1,2,4]triazolo[1,5-a]pyrazin-2-yl}ethynyl)-1-methyl-1H-imidazol-4-yl]pyrrolidin-2-one
1-[1-(Cyclopropylmethyl)-2-(2-{5,8-dimethyl-[1,2,4]triazolo[1,5-c]pyrimidin-2-yl}ethyl)-1H-imidazol-4-yl]pyrrolidin-2-one
1-[2-[2-(5,8-dimethyl-[1,2,4]triazolo[1,5-c]pyrimidin-2-yl) ethyl]-1-phenyl-imidazol-4-yl]pyrrolidin-2-one
1-[2-(2-{5,8-Dimethyl-[1,2,4]triazolo[1,5-c]pyrimidin-2-yl}ethyl)-1-(2,2,2-trifluoroethyl)-1H-imidazol-4-yl]pyrrolidin-2-one
1-[1-(2,2-difluoroethyl)-2-(2-{5,8-dimethyl-[1,2,4]triazolo[1,5-c]pyrimidin-2-yl}ethyl)-1 H-imidazol-4-yl]pyrrolidin-2-one
1-{2-[(E)-2-{4,7-Dimethyl-[1,2,4]triazolo[1,5-a]pyrazin-2-yl}ethenyl]-1-phenyl-1H-imidazol-4-yl}pyrrolidin-2-one
1-[2-(2-{5,7-dimethyl-[1,2,4]triazolo[1,5-a]pyrimidin-2-yl}ethyl)-1-methyl-1H-imidazol-4-yl]pyrrolidin-2-one
1-(2-{2-[3-Methyl-2-(trifluoromethyl)imidazo[1,2-b]pyridazin-6-yl]ethyl}-1-phenyl-1H-imidazol-4-yl)pyrrolidin-2-one
1-(1-Methyl-2-{2-[3-methyl-2-(trifluoromethyl) imidazo[1, 2-b]pyridazin-6-yl]ethynyl}-1H-imidazol-4-yl)pyrrolidin-2-one
1-(2-{2-[3-methyl-2-(trifluoromethyl) imidazo[1, 2-b]pyridazin-6-yl]ethynyl}-1-phenyl-1H-imidazol-4-yl) pyrrolidin-2-one
N,3-Dimethyl-6-{2-[1-methyl-4-(2-oxopyrrolidin-1-yl)-1H-imidazol-2-yl]ethyl}-2-trifluoromethyl)imidazo[1,2-b]pyridazine-8-carboxamide
N,3-Dimethyl-6-{2-[4-(2-oxopyrrolidin-1-yl)-1-phenyl-1H-imidazol-2-yl]ethyl}-2-(trifluoromethyl)imidazo[1,2-b]pyridazine-8-carboxamide The present invention relates to a process for the manufacture of a compound of formula (I), comprising:
a) reacting a compound of formula (II)

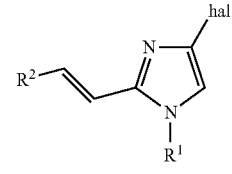

b) with a compound of formula (III) or (IV),

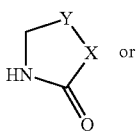
(III)

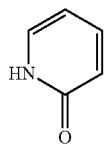
(IV)

to a compound of formula (I) and optionally hydrogenation, wherein $R^1$, $R^2$, X and Y are as defined hereinbefore.

10. A process for the manufacture of a compound of formula I, wherein B is ethynylen comprising:

a) reacting a compound of formula (V)

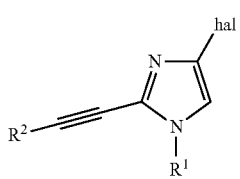

b) with a compound of formula (III) or (IV),

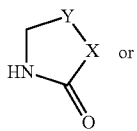
(III)

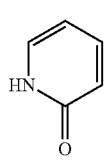
(IV)

to a compound of formula (I), wherein $R^1$, $R^2$, X and Y are as defined hereinbefore.

In another aspect the invention relates to the use of compounds of the invention for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

In another aspect the invention relates to the use of a compound of the invention for the preparation of a medicament for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

In another aspect the invention relates to a compound of the invention for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

In another aspect the invention relates to a method for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer, which method comprises administering an effective amount of a compound of the invention to a subject in need thereof.

General Procedures

Compounds of general formula (1a), (1b) and (1c) can be prepared as outlined in Scheme 1.

Scheme 1

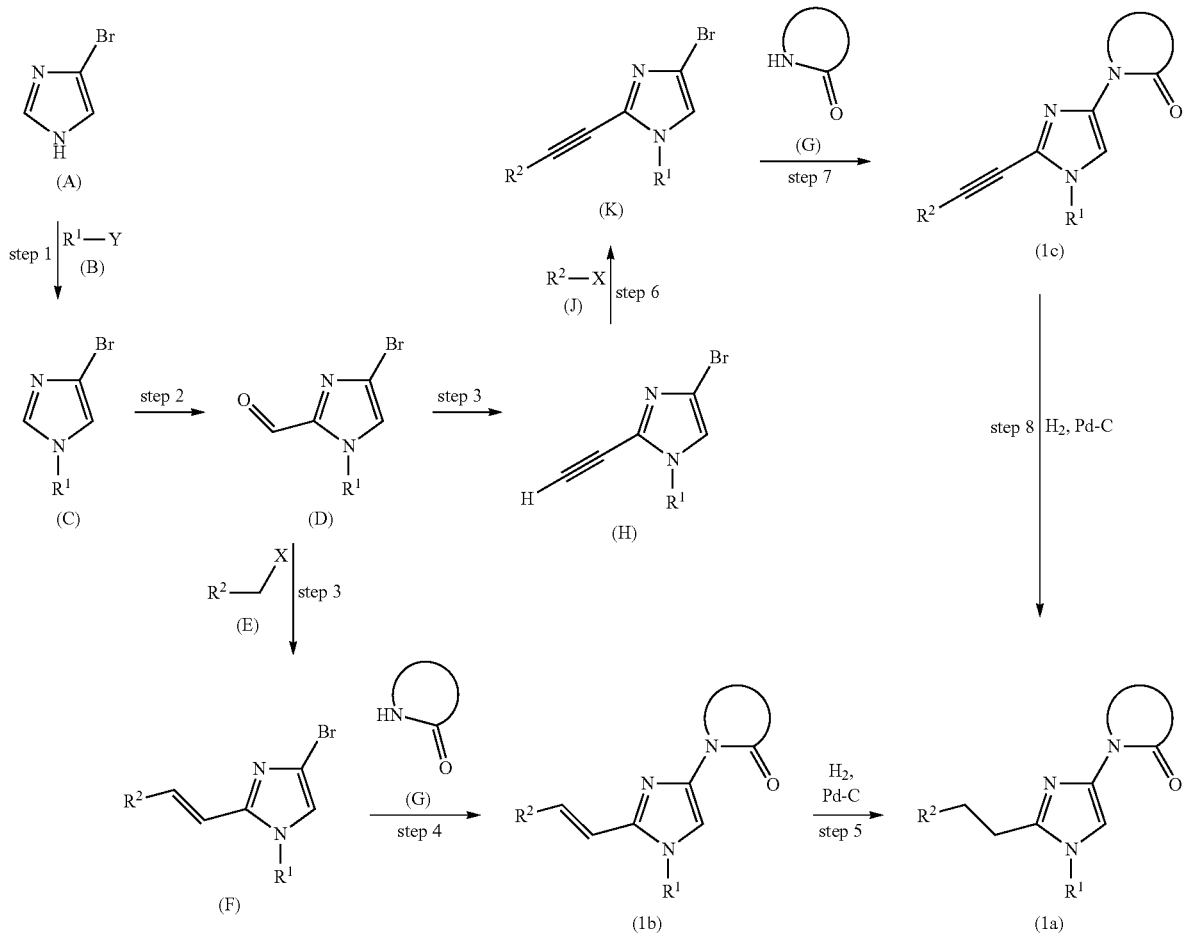

Compounds of general formula (1b) can be prepared by Wittig reaction between aldehyde (D) and Wittig salt (E) (step 3) in the presence of a suitable base such as DBU in a solvent such as THF, EtOH or mixtures thereof, followed by transition-metal catalyzed coupling with amide (G) using a copper source such as Cu(I)I, a palladium catalyst such as tris(dibenzylideneacetone)dipalladium(0), a base such as cesium carbonate and a polar solvent such as dioxane, DMF and water (step 4). Compounds of formula (1a) are obtained by subsequent hydrogenation (step 5) at ambient pressure (balloon) using a catalyst such as Pd/C, Raney nickel or Lindlar in a solvent such as EtOH or MeOH (Scheme 1).

Alternatively, compounds of formula (1a) are obtained by hydrogenation (step 8) of compounds of formula (1c) at ambient pressure (balloon) using a catalyst such as Pd/C, Raney nickel or Lindlar in a solvent such as EtOH or MeOH (Scheme 1).

Compounds of general formula (1c) can be prepared by Sonogashira reaction between an heteroaromatic halogenide (J) and alkyne (H) using a copper source such as Cu(I)I, a palladium catalyst such as bis(triphenylphosphine)palladium(II) chloride, a base such as triethylamine and a polar solvent such as DMF (step 6). Elevated temperature and prolonged reaction time was required, especially, when chlorides were used as starting material.

Compounds of formula (H) can be prepared from compound (D) as described in Scheme 1 and in the experimental part below as well as by literature-known methods.

Compounds of formula (A), (B), (C), (D), (E), (G) and (J) are commercial or can be prepared as described in the experimental part below or by literature-known methods familiar to those skilled in the art.

Alternatively, compounds of formula (D) can be prepared from compounds of formula (A) by introducing a protecting-group such as triphenylmethyl (step 9), introduction of the aldehyde function in the same manner as outlined in scheme 1, step 2 (step 10), deprotection of the nitrogen with a suitable reagent like acetic acid (step 11) and final reaction with a reagent of formula (B) using a base such as cesium carbonate and a polar solvent such as DMF (step 12). Suitable protecting groups and conditions for introduction and removal are literature-known or familiar to those skilled in the art.

Scheme 2

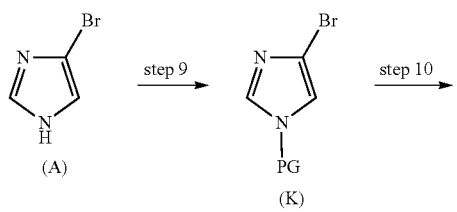

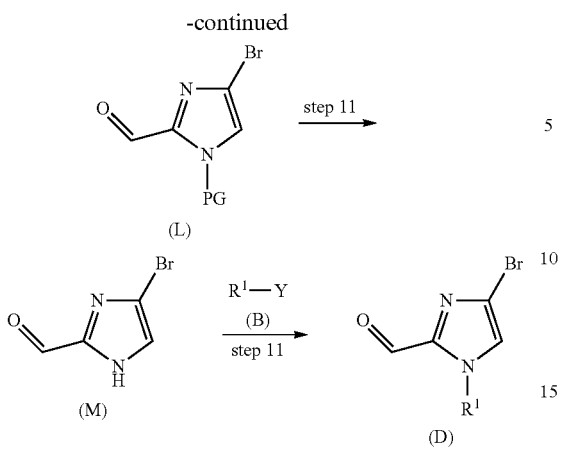

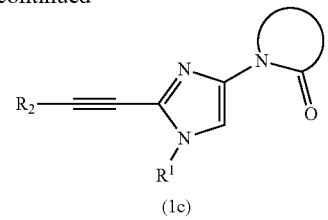

Another method of preparing compounds of formula (1c) comprises a Sonogashira reaction between an heteroaromatic halogenide (J) and alkyne (O) using a copper source such as Cu(I)I, a palladium catalyst such as bis(triphenylphosphine)palladium(II) chloride, a base such as triethylamine and a polar solvent such as DMF (step 15). The compounds of formula (O) can be prepared by coupling a compound of formula (D) with an amide of formula (G) using a transition-metal catalyst such tris(dibenzylideneacetone)dipalladium(0), a copper source such as Cu(I)I, a base such as cesium carbonate and a polar solvent such as dioxane, DMF and water (step 13) followed by reaction with dimethyl (1-diazo-2-oxopropyl)phosphonate (step 14).

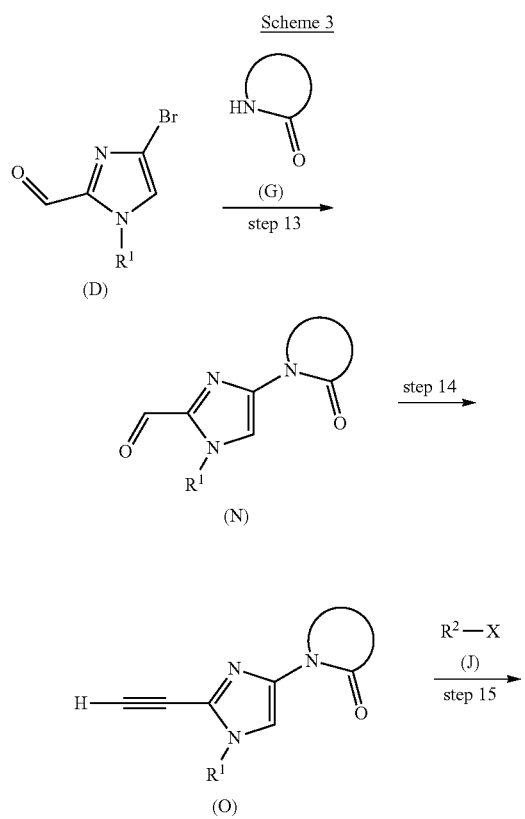

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments.

In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit PDE10 and to control the cAMP signaling pathway. For example, such amount may be below the amount that is toxic to normal cells, or the mammal as a whole.

In one example, the pharmaceutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, preferably contain from about 25-100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula (I), or a stereoisomer or pharmaceutically acceptable salt thereof. In a further embodiment includes a pharmaceutical composition comprising a compound of Formula (I), or a stereoisomer or pharmaceutically acceptable salt thereof, together with a pharmaceutically acceptable carrier or excipient.

The human PDE10A full length assay was performed in 96-well micro titer plates. The reaction mixture of 50 µl contained 20 mM HEPES pH=7.5/10 mM $MgCl_2$/0.05 mg/ml BSA (Sigma cat. #A-7906), 50 nM cGMP (Sigma, cat. #G6129) and 50 nM [3H]-cGMP (GE Healthcare, cat. #TRK392 S.A. 13.2 Ci/mmol), 3.75 ng/well PDE10A enzyme (Enzo Life Science, Lausen, Switzerland cat #SE-534) with or without a specific test compound. A range of concentrations of the potential inhibitor was used to generate data for calculating the concentration of inhibitor resulting in 50% of the effect (e.g. IC50, the concentration of the competitor inhibiting PDE10A activity by 50%). Non-specific activity was tested without the enzyme. The reaction was initiated by the addition of the substrate solution (cGMP and [3H]-cGMP) and allowed to progress for 20 minutes at room temperature. The reaction was terminated by adding 25 µl of YSi-SPA scintillation beads (GE Healthcare, cat. # RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer TopCount Scintillation plate reader.

The compounds according to formula (I) have an IC50 value below 10 µM, more specifically below 5 µM, yet more specifically below 1 µM. The following table shows data for some examples.

| Example | PDE10A inhibition IC50 [µM] |
| --- | --- |
| 1 | 0.039 |
| 2 | 0.0013 |
| 3 | 0.0095 |
| 4 | 0.15 |
| 5 | 0.195 |
| 6 | 0.081 |
| 7 | 0.027 |
| 8 | 0.162 |
| 9 | 0.0046 |
| 10 | 0.0546 |
| 11 | 0.018 |
| 12 | 0.0169 |
| 13 | 0.0367 |
| 14 | 0.0469 |
| 15 | 0.0290 |
| 16 | 0.0148 |
| 17 | 0.0032 |
| 18 | 0.1679 |
| 19 | 0.0268 |
| 20 | 0.0194 |
| 21 | 0.1761 |
| 22 | 0.1168 |
| 23 | 0.0031 |
| 24 | 0.0755 |
| 25 | 0.0219 |
| 26 | 0.1121 |
| 27 | 0.0029 |

EXAMPLES

Example 1

1-(2-(2-(5,8-dimethyl-[1,2,4]triazolo[1,5-c]pyrimidin-2-yl)ethyl)-1-methyl-1H-imidazol-4-yl)pyrrolidin-2-one

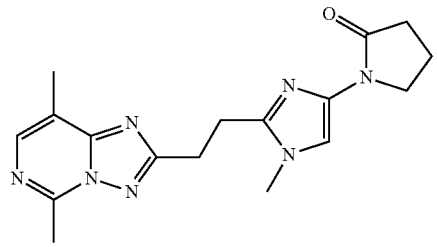 [SMILES: Cc1cnc(C)n2nc(CCc3nc(N4CCCC4=O)cn3C)nc12]

a) (5,8-Dimethyl-[1,2,4]triazolo[1,5-c]pyrimidin-2-ylmethyl)-triphenyl-phosphonium chloride

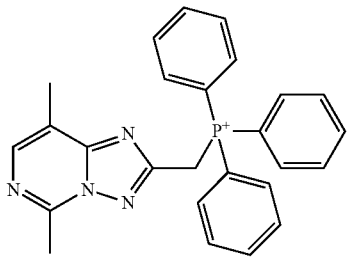 [SMILES: Cc1cnc(C)n2nc(C[P+](c3ccccc3)(c3ccccc3)c3ccccc3)nc12]

A mixture of 2-(chloromethyl)-5,8-dimethyl-[1,2,4]triazolo[1,5-c]pyrimidine (prepared as described in US2012/178748) (2.254 g, 11.5 mmol, Eq: 1.00) and triphenylphosphine (3.01 g, 11.5 mmol, Eq: 1.00) in acetonitrile (143 ml) was refluxed for 23.5 h under argon atmosphere. The solvent was evaporated and the solid was triturated with ether, the solid was filtered off, washed with ether and dried under high vacuum affording (5,8-Dimethyl-[1,2,4]triazolo[1,5-c]pyrimidin-2-ylmethyl)-triphenyl-phosphonium chloride (3.959 g, 75.3%) as light brown powder. MS-Cl: m/z=423.6 (M+H+)

b) 4-Bromo-1-methyl-1H-imidazole-2-carbaldehyde

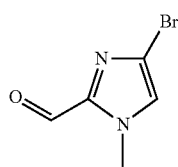

n-buthyllithium 1.6M in hexane (1.83 ml, 2.93 mmol, Eq: 1.05) was stirred in Diethyl ether (2.5 ml) and cooled to −78° C. in a dry-ice bath. 4-bromo-1-methyl-1H-imidazole (450 mg, 2.8 mmol, Eq: 1.00) solved in Diethyl ether (0.75 ml) was added via syringe in ca. 4-5 portions over 20 min. After stirring for ca. 60 min at −78° C., DMF (215 mg, 226 µl, 2.93 mmol, Eq: 1.05) in Diethyl ether (0.5 ml) was added via syringe in portions over ca. 15 min. The reaction mixture was stirred at −78° C. for 2.5 h. Water was added and extracted three times with ethyl acetate, dried over magnesium sulfate, filtered and evaporated. The crude material was purified by column chromatography using heptane/ethyl acetate (0-100% ethyl acetate) as eluent affording 4-Bromo-1-methyl-1H-imidazole-2-carbaldehyde (326 mg, 61.7%) as light yellow solid. MS: m/z=191.3 (M+H+)

b) 2-[(E)-2-(4-Bromo-1-methyl-1H-imidazol-2-yl)-vinyl]-5,8-dimethyl-[1,2,4]triazolo[1,5-c]pyrimidine

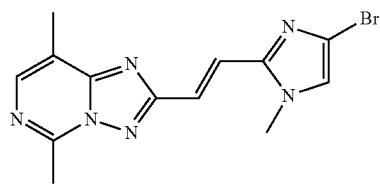 [SMILES: Cc1cnc(C)n2nc(/C=C/c3nc(Br)cn3C)nc12]

To a solution of 4-bromo-1-methyl-1H-imidazole-2-carbaldehyde (50 mg, 265 µmol, Eq: 1.00) in tetrahydrofuran (5 ml) were added ((5,8-dimethyl-[1,2,4]triazolo[1,5-c]pyrimidin-2-yl)methyl)triphenylphosphonium chloride (121 mg, 265 µmol, Eq: 1) and DBU (44.3 mg, 43.9 µl, 291 µmol, Eq: 1.1). The reaction mixture was stirred for 18 hours at 25° C. The crude material was applied on silica gel and purified by flash chromatography over silica gel column using ethyl acetate/methanol 0-10% as eluent affording 2-[(E)-2-(4-Bromo-1-methyl-1H-imidazol-2-yl)-vinyl]-5,8-dimethyl-[1,2,4]triazolo[1,5-c]pyrimidine (73 mg 82.8%) as white solid. MS: m/z=333.1 (M+H+)

c) 1-{2-[(E)-2-(5,8-Dimethyl-[1,2,4]triazolo[1,5-c]pyrimidin-2-yl)-vinyl]-1-methyl-1H-imidazol-4-yl}-pyrrolidin-2-one

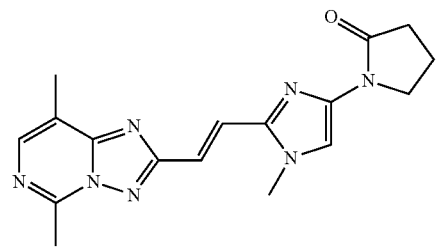 [SMILES: Cc1cnc(C)n2nc(/C=C/c3nc(N4CCCC4=O)cn3C)nc12]

A mixture of (E)-2-(2-(4-bromo-1-methyl-1H-imidazol-2-yl)vinyl)-5,8-dimethyl-[1,2,4]triazolo[1,5-c]pyrimidine (70 mg, 210 µmol, Eq: 1.00), pyrrolidin-2-one (35.8 mg, 32.2 µl, 420 µmol, Eq: 2), cesium carbonate (137 mg, 420 µmol, Eq: 2), tris(dibenzylideneacetone)dipalladium(0)/Pd2(dba)3 (3.85 mg, 4.2 µmol, Eq: 0.02) and 4,5-bis(diphenylphosphino)-9,9-dimethylxanthene (xant-phos) (4.86 mg, 8.4 µmol, Eq: 0.04) in dioxane (3.5 ml) was heated in a closed vessel to 140° C. tris(dibenzylideneacetone)dipalladium(0)/Pd2(dba)3 (3.85 mg, 4.2 µmol, Eq: 0.02) and 4,5-bis(diphenylphosphino)-9,9-dimethylxanthene (xant-phos) (4.86 mg, 8.4 µmol, Eq: 0.04) was added again and stirring was continued for 4 h. The crude material was applied on silica gel and purified by column chromatography using ethyl acetate/methanol (0-10% methanol) as eluent affording 1-{2-[(E)-2-(5,8-Dimethyl-[1,2,4]triazolo[1,5-c]pyrimidin-2-yl)-vinyl]-1-methyl-1H-imidazol-4-yl}-pyrrolidin-2-one (24 mg, 33.9%) as light yellow solid. MS: m/z=337 (M+)

d) 1-{2-[(E)-2-(5,8-Dimethyl-[1,2,4]triazolo[1,5-c]pyrimidin-2-yl)-vinyl]-1-methyl-1H-imidazol-4-yl}-pyrrolidin-2-one

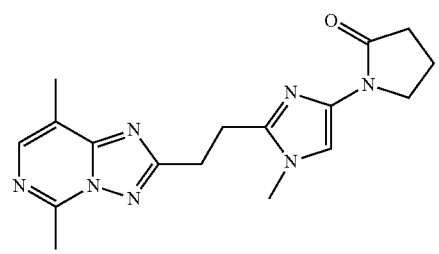 [SMILES: Cc1cnc(C)n2nc(CCc3nc(N4CCCC4=O)cn3C)nc12]

(E)-1-(2-(2-(5,8-dimethyl-[1,2,4]triazolo[1,5-c]pyrimidin-2-yl)vinyl)-1-methyl-1H-imidazol-4-yl)pyrrolidin-2-one (20 mg, 59.3 μmol, Eq: 1.00) was stirred in Methanol (2 ml) with palladium on carbon 10% (6.31 mg, 5.93 μmol, Eq: 0.1) under a hydrogen atmosphere at room temperature overnight. The crude material was applied on silica gel and purified by column chromatography using ethyl acetate/methanol (0-10%) methanol as eluent affording 1-{2-[2-(5,8-Dimethyl-[1,2,4]triazolo[1,5-c]pyrimidin-2-yl)-ethyl]-1-methyl-1H-imidazol-4-yl}-pyrrolidin-2-one (7.7 mg, 38.3%) as white solid. MS: m/z=340.5 (M+H+)

Example 2

1-(2-(2-(5,8-dimethyl-[1,2,4]triazolo[1,5-a]pyrazin-2-yl)ethyl)-1-phenyl-1H-imidazol-4-yl)pyrrolidin-2-one

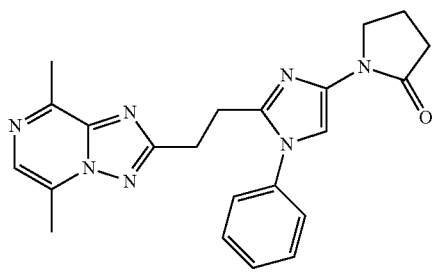

a) (5,8-Dimethyl-[1,2,4]triazolo[1,5-a]pyrazin-2-ylmethyl)-triphenyl-phosphonium chloride

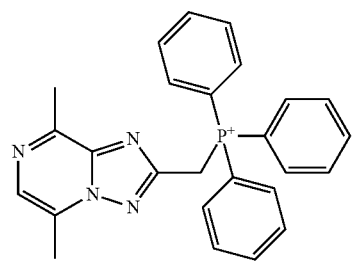 [SMILES: Cc1ncc(C)n2nc(C[P+](c3ccccc3)(c3ccccc3)c3ccccc3)nc12]

Was prepared in the same manner as described in Example 1a) 2-(chloromethyl)-5,8-dimethyl-[1,2,4]triazolo[1,5-a]pyrazine (prepared as described in US2012/178748) (3.259 g, 16.6 mmol, Eq: 1.00) affording ((5,8-dimethyl-[1,2,4]triazolo[1,5-a]pyrazin-2-ylmethyl)triphenyl-phosphonium (11.5 g, 98.5%) as a light brown solid. MS-Cl: m/z=423.4 (M+H+)

b) 4-Bromo-1-phenyl-1H-imidazole

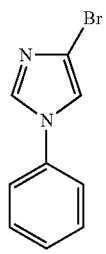

A mixture of 4-bromo-1H-imidazole (3000 mg, 20.4 mmol, Eq: 1.00), iodobenzene (3.75 g, 2.05 ml, 18.4 mmol, Eq: 0.9), copper (I) iodide (194 mg, 1.02 mmol, Eq: 0.05), 8-hydroxyquinoline (148 mg, 1.02 mmol, Eq: 0.05) and cesium carbonate (8.85 g, 27.1 mmol, Eq: 1.33) was dissolved in DMF (45.0 ml) and water (4.5 ml). The mixture was stirred for 2.5 days at 130° C. The residue was diluted with ethyl acetate and washed with water, ammonium chloride sol. sat. and sodiumhydrogen carbonate sat. The organic layer was separated, dried over magnesium sulfate, filtrated and evaporated. The crude material was applied on silica gel and purified by flash chromatography over a 70 g silica gel column using heptane/ethyl acetate 10-30% as eluent affording 4-Bromo-1-phenyl-1H-imidazole (2.345 g, 51.5%) as off-white solid. MS: m/z=222.98 (M+)

c) 4-Bromo-1-phenyl-1H-imidazole-2-carbaldehyde

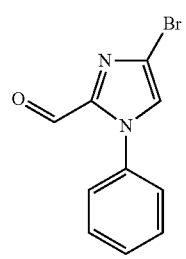 [SMILES: O=Cc1nc(Br)cn1-c1ccccc1]

n-buthyllithium 1.6M in hexane (6.9 ml, 11.0 mmol, Eq: 1.05) was stirred in THF (12.0 ml) and cooled to −78° C. in a dry-icebath. 4-bromo-1-phenyl-1H-imidazole/RO7016494-000-002 (2.345 g, 10.5 mmol, Eq: 1.00) solved in THF (3.59 ml) was added via syringe in ca. 4-5 portions over 20 min. After stirring for ca. 60 min at −78° C., DMF (807 mg, 849 μl, 11.0 mmol, Eq: 1.05) in THF (2.39 ml) was added via syringe in portions over ca. 15 min. The reaction mixture was stirred at −78° C. for 2.5 h. Water was added and extracted three times with ethyl acetate, dried over magnesium sulfate, filtered and evaporated. The crude material was applied on silica gel and purified by flash chromatography using heptane/ethyl acetate 10-30% as eluent affording 4-Bromo-1-phenyl-1H-imidazole-2-carbaldehyde (1.461 g, 55.4%) as a light yellow solid. MS: m/z=251.1 (M+H+)

d) 2-[(E)-2-(4-Bromo-1-phenyl-1H-imidazol-2-yl)-vinyl]-5,8-dimethyl-[1,2,4]triazolo[1,5-a]pyrazine

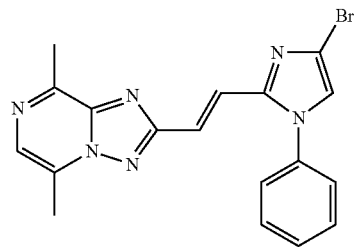 [SMILES: Cc1ncc(C)n2nc(/C=C/c3nc(Br)cn3-c3ccccc3)nc12]

Was prepared in the same manner as described in Example 1c) using ((5,8-dimethyl-[1,2,4]triazolo[1,5-a]pyrazin-2-yl)methyl)triphenylphosphonium chloride (1.16 g, 2.53 mmol, Eq: 1.00) and 4-bromo-1-phenyl-1H-imidazole-2-carbaldehyde (635 mg, 2.53 mmol, Eq: 1.00) as starting materials affording 2-[(E)-2-(4-Bromo-1-phenyl-1H-imidazol-2-yl)-vinyl]-5,8-dimethyl-[1,2,4]triazolo[1,5-a]pyrazine (278 mg, 27.8%) as a white solid. MS: m/z=395.2 (M+H+)

e) 1-{2-[(E)-2-(5,8-Dimethyl-[1,2,4]triazolo[1,5-a]pyrazin-2-yl)-vinyl]-1-phenyl-1H-imidazol-4-yl}-pyrrolidin-2-one

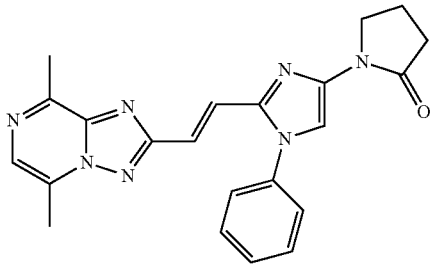 [SMILES: Cc1ncc(C)n2nc(/C=C/c3nc(N4CCCC4=O)cn3-c3ccccc3)nc12]

Was prepared in the same manner as described in Example 1d) using (E)-2-(2-(4-bromo-1-phenyl-1H-imidazol-2-yl)vinyl)-5,8-dimethyl-[1,2,4]triazolo[1,5-a]pyrazine (80 mg, 202 µmol, Eq: 1.00) and pyrrolidin-2-one (34.5 mg, 31.0 µl, 405 µmol, Eq: 2), cesium carbonate (198 mg, 607 µmol, Eq: 3) as starting materials affording 1-{2-[(E)-2-(5,8-Dimethyl-[1,2,4]triazolo[1,5-a]pyrazin-2-yl)-vinyl]-1-phenyl-1H-imidazol-4-yl}-pyrrolidin-2-one (80.8 mg, 18.8%) as a light yellow solid. MS: m/z=400.3 (M+H+)

f) 1-{2-[2-(5,8-Dimethyl-[1,2,4]triazolo[1,5-a]pyrazin-2-yl)-ethyl]-1-phenyl-1H-imidazol-4-yl}-pyrrolidin-2-one

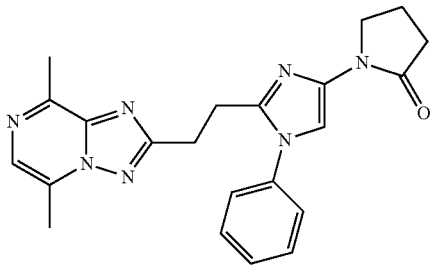 [SMILES: Cc1ncc(C)n2nc(CCc3nc(N4CCCC4=O)cn3-c3ccccc3)nc12]

Was prepared in the same manner as described in Example 1d) using (E)-1-(2-(2-(5,8-dimethyl-[1,2,4]triazolo[1,5-a]pyrazin-2-yl)vinyl)-1-phenyl-1H-imidazol-4-yl)pyrrolidin-2-one (13 mg, 32.5 µmol, Eq: 1.00) as starting material affording 1-{2-[2-(5,8-Dimethyl-[1,2,4]triazolo[1,5-a]pyrazin-2-yl)-ethyl]-1-phenyl-1H-imidazol-4-yl}-pyrrolidin-2-one (7 mg, 53.6%) as white solid. MS: m/z=402.4 (M+H+)

Example 3

1-[2-[(E)-2-(5,8-dimethyl-[1,2,4]triazolo[1,5-a]pyrazin-2-yl)ethenyl]-1-phenylimidazol-4-yl]pyrrolidin-2-one

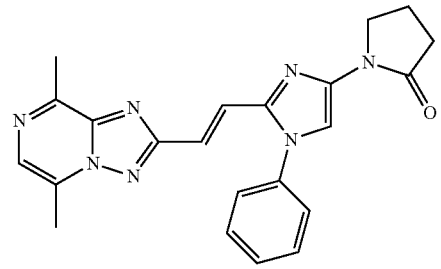 [SMILES: Cc1ncc(C)n2nc(/C=C/c3nc(N4CCCC4=O)cn3-c3ccccc3)nc12]

Was prepared as described in Example 2e). MS: m/z=400.3 (M+H+)

Example 4

1-(1-(Cyclopropylmethyl)-2-(2-(5, 8-dimethyl-[1,2,4]triazolo[1,5-a]pyrazin-2-yl)ethyl)-1H-imidazol-4-yl)pyridin-2(1H)-one

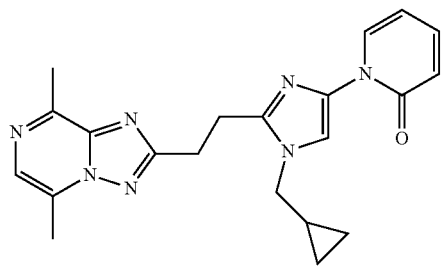 [SMILES: Cc1ncc(C)n2nc(CCc3nc(-n4ccccc4=O)cn3CC3CC3)nc12]

a) 4-bromo-1-(cyclopropylmethyl)-1H-imidazole

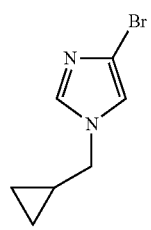

Was prepared in the same manner as described in Example 2b) using 4-bromo-1H-imidazole (2.38 g, 16.2 mmol, Eq: 1.00) and (iodomethyl)cyclopropane (4.91 g, 16.2 mmol, Eq: 1) as starting material, affording 4-bromo-1-(cyclopropylmethyl)-1H-imidazole (980 mg, 24.1%) as orange oil. MS: m/z=201 (M+H+)

b) 4-bromo-1-(cyclopropylmethyl)-1H-imidazole-2-carbaldehyde

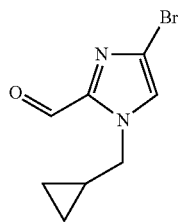 [SMILES: O=Cc1nc(Br)cn1CC1CC1]

Was prepared in the same manner as described in Example 2c) using 4-bromo-1-(cyclopropylmethyl)-1H-imidazole (258 mg, 1.28 mmol, Eq: 1.00) as starting material, affording 4-bromo-1-(cyclopropylmethyl)-1H-imidazole-2-carbaldehyde (114 mg, 38.8%) as light yellow oil. MS: m/z=229.0 (M+H+)

c) 2-[(E)-2-(4-Bromo-1-cyclopropylmethyl-1H-imidazol-2-yl)-vinyl]-5,8-dimethyl-[1,2,4]triazolo[1,5-a]pyrazine

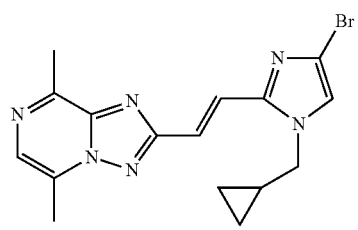

Was prepared in the same manner as described in Example 1c) using ((5,8-dimethyl-[1,2,4]triazolo[1,5-a]pyrazin-2-yl)methyl)triphenylphosphonium chloride (228 mg, 497 µmol, Eq: 1.00) and 4-bromo-1-(cyclopropylmethyl)-1H-imidazole-2-carbaldehyde (114 mg, 498 µmol, Eq: 1.00) as starting material, affording 2-[(E)-2-(4-Bromo-1-cyclopropylmethyl-1H-imidazol-2-yl)-vinyl]-5,8-dimethyl-[1,2,4]triazolo[1,5-a]pyrazine (479 mg, 58.9%) as yellow solid. MS: m/z=375.2 (M+H+)

d) 1-{1-Cyclopropylmethyl-2-[(E)-2-(5,8-dimethyl-[1,2,4]triazolo[1,5-a]pyrazin-2-yl)vinyl]-1H-imidazol-4-yl}-1H-pyridin-2-one

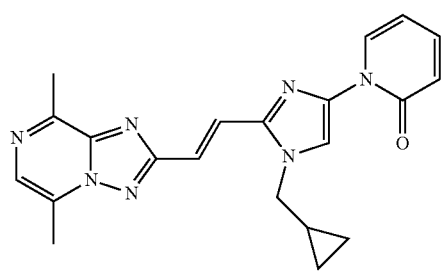 [SMILES: Cc1ncc(C)n2nc(/C=C/c3nc(-n4ccccc4=O)cn3CC3CC3)nc12]

A mixture of (E)-2-(2-(4-bromo-1-(cyclopropylmethyl)-1H-imidazol-2-yl)vinyl)-5,8-dimethyl-[1,2,4]triazolo[1,5-a]pyrazine (50 mg, 134 µmol, Eq: 1.00), pyridin-2(3H)-one (25.5 mg, 268 µmol, Eq: 2), cesium carbonate (87.3 mg, 268 µmol, Eq: 2), copper(I)iodide (6.13 mg, 6.7 µmol, Eq: 0.05) and 8-hydroxyquinoline (3.88 mg, 6.7 µmol, Eq: 0.05) in DMF (350 µl) and water (35.0 µl) was heated in a closed vessel for 1 h at 140° C. The crude material was applied on silica gel and purified by column chromatography using ethyl acetate/methanol (0-10% methanol). Still not pure. The material was purified by prep HPLC affording 1-{1-Cyclopropylmethyl-2-[(E)-2-(5,8-dimethyl-[1,2,4]triazolo[1,5-a]pyrazin-2-yl)-vinyl]-1H-imidazol-4-yl}-1H-pyridin-2-one (15 mg, 28.9%) as light yellow solid. MS: m/z=388.2 (M+H+)

e) 1-{1-Cyclopropylmethyl-2-[2-(5,8-dimethyl-[1,2,4]triazolo[1,5-a]pyrazin-2-yl)-ethyl]-1H-imidazol-4-yl}-1H-pyridin-2-one

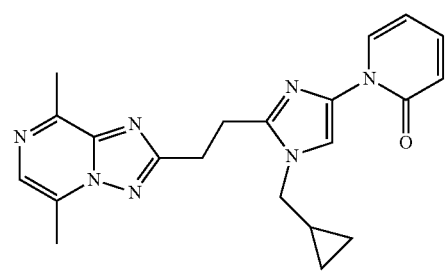 [SMILES: Cc1ncc(C)n2nc(CCc3nc(-n4ccccc4=O)cn3CC3CC3)nc12]

Was prepared in the same manner as described in Example 1d) using (E)-1-(1-(cyclopropylmethyl)-2-(2-(5,8-dimethyl-[1,2,4]triazolo[1,5-a]pyrazin-2-yl)vinyl)-1H-imidazol-4-yl)pyridin-2(1H)-one (13 mg, 33.6 µmol, Eq: 1.00) as starting material affording 1-{1-Cyclopropylmethyl-2-[2-(5,8-dimethyl-[1,2,4]triazolo[1,5-a]pyrazin-2-yl)-ethyl]-1H-imidazol-4-yl}-1H-pyridin-2-one (4.06 mg, 31.1%) as off-white solid. MS: m/z=390.3 (M+H+)

Example 5

1-(2-(2-(5,8-dimethyl-[1,2,4]triazolo[1,5-a]pyrazin-2-yl)ethyl)-1-methyl-1H-imidazol-4-yl)pyridin-2(1H)-one

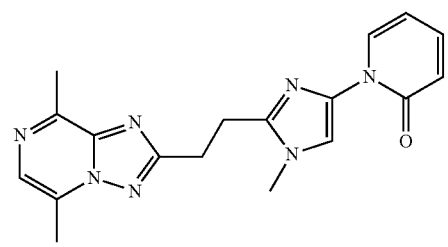 [SMILES: Cc1ncc(C)n2nc(CCc3nc(-n4ccccc4=O)cn3C)nc12]

a) 2-[(E)-2-(4-Bromo-1-methyl-1H-imidazol-2-yl)-vinyl]-5,8-dimethyl-[1,2,4]triazolo[1,5-a]pyrazine

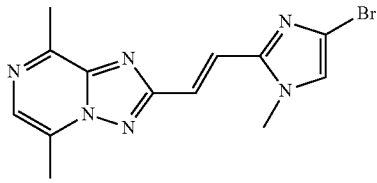 [SMILES: Cc1ncc(C)n2nc(/C=C/c3nc(Br)cn3C)nc12]

Was prepared in the same manner as described in Example 1c) using 4-bromo-1-methyl-1H-imidazole-2-carbaldehyde (350 mg, 1.85 mmol, Eq: 1.00) and ((5,8-dimethyl-[1,2,4]triazolo[1,5-a]pyrazin-2-yl)methyl)triphenylphosphonium chloride (850 mg, 1.85 mmol, Eq: 1) as starting material, affording 2-[(E)-2-(4-Bromo-1-methyl-1H-imidazol-2-yl)-vinyl]-5,8-dimethyl-[1,2,4]triazolo[1,5-a]pyrazine (480 mg, 77.8%) as white solid. MS: m/z=333.3 (M+H+)

b) 1-{2-[(E)-2-(5,8-Dimethyl-[1,2,4]triazolo[1,5-a]pyrazin-2-yl)-vinyl]-1-methyl-1H-imidazol-4-yl}-1H-pyridin-2-one

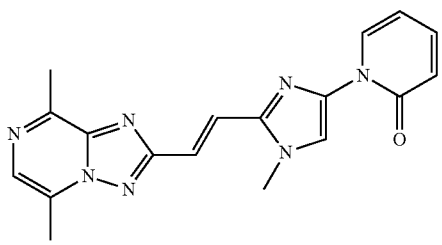 [SMILES: Cc1ncc(C)n2nc(/C=C/c3nc(-n4ccccc4=O)cn3C)nc12]

Was prepared in the same manner as described in Example 4d) using (E)-2-(2-(4-bromo-1-methyl-1H-imidazol-2-yl)vinyl)-5,8-dimethyl-[1,2,4]triazolo[1,5-a]pyrazine (50 mg, 150 µmol, Eq: 1.00) and pyridin-2(3H)-one (28.5 mg, 300 µmol, Eq: 2) as starting material, affording 1-{2-[(E)-2-(5,8-Dimethyl-[1,2,4]triazolo[1,5-a]pyrazin-2-yl)-vinyl]-1-methyl-1H-imidazol-4-yl}-1H-pyridin-2-one (22.3 mg, 42.8%) as light yellow solid. MS: m/z=348.16 (M+H+)

c) 1-{2-[2-(5,8-Dimethyl-[1,2,4]triazolo[1,5-a]pyrazin-2-yl)-ethyl]-1-methyl-1H-imidazol-4-yl}-1H-pyridin-2-one

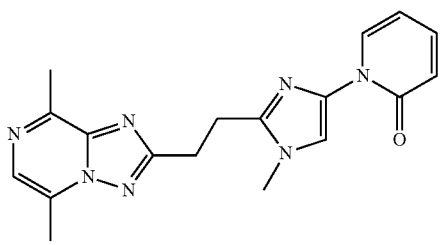 [SMILES: Cc1ncc(C)n2nc(CCc3nc(-n4ccccc4=O)cn3C)nc12]

Was prepared in the same manner as described in Example 1d) using (E)-1-(2-(2-(5,8-dimethyl-[1,2,4]triazolo[1,5-a]pyrazin-2-yl)vinyl)-1-methyl-1H-imidazol-4-yl)pyridin-2(1H)-one (22 mg, 63.3 µmol, Eq: 1.00) as starting material, affording 1-{2-[2-(5,8-Dimethyl-[1,2,4]triazolo[1,5-a]pyrazin-2-yl)-ethyl]-1-methyl-1H-imidazol-4-yl}-1H-pyridin-2-one (1.6 mg, 7.23%) as white solid. MS: m/z=350.3 (M+H+)

Example 6

1-[1-cyclopropyl-2-[(E)-2-(5,8-dimethyl-[1,2,4]triazolo[1,5-a]pyrazin-2-yl)ethenyl]imidazol-4-yl]pyrrolidin-2-one

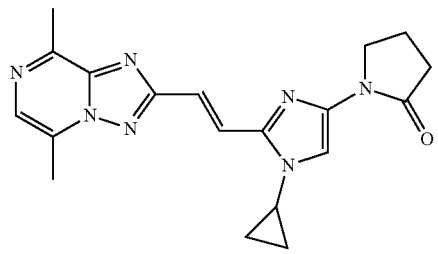 [SMILES: Cc1ncc(C)n2nc(/C=C/c3nc(N4CCCC4=O)cn3C3CC3)nc12]

a) 4-Bromo-1-cyclopropyl-1H-imidazole

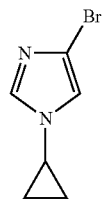

A mixture of 4-bromo-1H-imidazole (1 g, 6.8 mmol, Eq: 1.00), cyclopropylboronic acid (1.17 g, 13.6 mmol, Eq: 2), copper(II) acetate (1.24 g, 6.8 mmol, Eq: 1.00), 2,2'-bipyridine (1.06 g, 6.8 mmol, Eq: 1) and potassium carbonate (1.88 g, 13.6 mmol, Eq: 2) in 1,2-dichloroethane (52.3 ml) was heated for 4 hours at 70° C. under argon. The reaction was diluted with 50 ml dichloromethane washed with water, HCl (1 µmol) and Na2CO3 sat. The organic layer was separated, dried over magnesium sulfate, filtrated and evaporated. The aqueous layer was made basic and extracted three times with 1,2-dichloromethane, dried over magnesium sulfate, filtered and combined with the first org. Phase. The solvent was evaporated under vacuum. The crude material was applied on silica gel and purified by flash chromatography over silica gel column, using dichloromethane/methanol 0-5% as eluent affording 4-Bromo-1-cyclopropyl-1H-imidazole (452 mg, 28.4%) as a brown oil. MS: m/z=186.98 (M+H+)

b) 4-Bromo-1-cyclopropyl-1H-imidazole-2-carbaldehyde

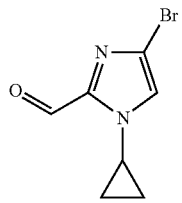 [SMILES: O=Cc1nc(Br)cn1C1CC1]

Was prepared in the same manner as described in Example 1b) using 4-bromo-1-cyclopropyl-1H-imidazole (452 mg, 2.42 mmol, Eq: 1.00) as starting material, affording 4-Bromo-1-cyclopropyl-1H-imidazole-2-carbaldehyde (257 mg, 49.5%) as off-white solid. MS: m/z=215.1 (M+H+)

c) 2-[(E)-2-(4-Bromo-1-cyclopropyl-1H-imidazol-2-yl)-vinyl]-5,8-dimethyl-[1,2,4]triazolo[1,5-a]pyrazine

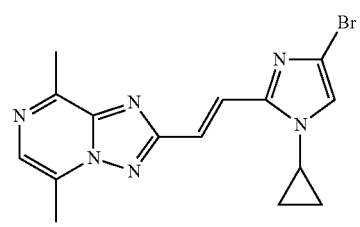 [SMILES: Cc1ncc(C)n2nc(/C=C/c3nc(Br)cn3C3CC3)nc12]

Was prepared in the same manner as described in Example 1c) using ((5,8-dimethyl-[1,2,4]triazolo[1,5-a]pyrazin-2-yl)methyl)triphenylphosphonium chloride (523 mg, 1.14 mmol, Eq: 1.00) and 4-bromo-1-cyclopropyl-1H-imidazole-2-carbaldehyde (245 mg, 1.14 mmol, Eq: 1.00) as starting material, affording 4-Bromo-1-cyclopropyl-1H-imidazole-2-carbaldehyde (340 mg, 83.1%) as white solid. MS: m/z=361.2 (M+H+)

d) 2-[(E)-2-(4-Bromo-1-cyclopropyl-1H-imidazol-2-yl)-vinyl]-5,8-dimethyl-[1,2,4]triazolo[1,5-a]pyrazine

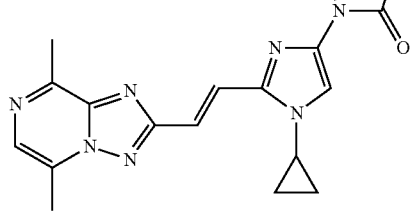

Was prepared in the same manner as described in Example 1d) using (E)-2-(2-(4-bromo-1-cyclopropyl-1H-imidazol-2-yl)vinyl)-5,8-dimethyl-[1,2,4]triazolo[1,5-a]pyrazine (110 mg, 306 µmol, Eq: 1.00) and pyrrolidin-2-one (52.1 mg, 47.0 µl, 612 µmol, Eq: 2) as starting material, affording 1-{2-[(E)-2-(5,8-Dimethyl-[1,2,4]triazolo[1,5-a]pyrazin-2-yl)-vinyl]-1-phenyl-1H-imidazol-4-yl}-pyrrolidin-2-one (39 mg, 35%) as yellow viscous oil. MS: m/z=364.3 (M+H+)

Example 7

1-{1-Cyclopropyl-2-[2-(5,8-dimethyl-[1,2,4]triazolo[1,5-a]pyrazin-2-yl)-ethyl]-1H-imidazol-4-yl}-pyrrolidin-2-one

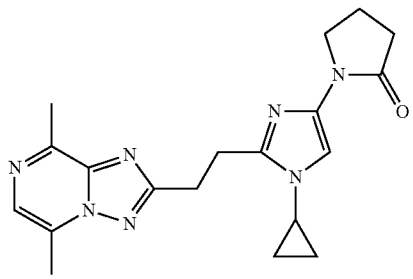 [SMILES: Cc1ncc(C)n2nc(CCc3nc(N4CCCC4=O)cn3C3CC3)nc12]

Was prepared in the same manner as described in Example 1d) using (E)-1-(1-cyclopropyl-2-(2-(5,8-dimethyl-[1,2,4]triazolo[1,5-a]pyrazin-2-yl)vinyl)-1H-imidazol-4-yl)pyrrolidin-2-one (35 mg, 96.3 µmol, Eq: 1.00) as starting material, affording 1-{1-Cyclopropyl-2-[2-(5,8-dimethyl-[1,2,4]triazolo[1,5-a]pyrazin-2-yl)-ethyl]-1H-imidazol-4-yl}-pyrrolidin-2-one (23.8 mg, 67.6%) as white solid. MS: m/z=366.3 (M+H+)

Example 8

2'-[(E)-2-(5,8-Dimethyl-[1,2,4]triazolo[1,5-a]pyrazin-2-yl)-vinyl]-3,1'-dimethyl-4,5-dihydro-3H,1'H-[1,4']biimidazolyl-2-one

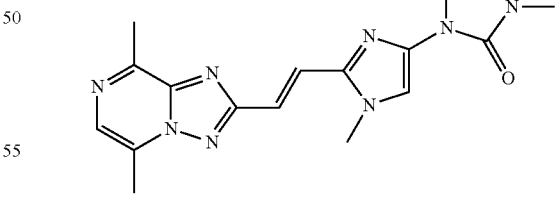

Was prepared in the same manner as described in Example 1d) using (E)-2-(2-(4-bromo-1-methyl-1H-imidazol-2-yl)vinyl)-5,8-dimethyl-[1,2,4]triazolo[1,5-a]pyrazine (50 mg, 150 µmol, Eq: 1.00) and 1-methylimidazolidin-2-one (30.0 mg, 300 µmol, Eq: 2) as starting material, affording 2'-[(E)-2-(5,8-Dimethyl-[1,2,4]triazolo[1,5-a]pyrazin-2-yl)-vinyl]-3,1'-dimethyl-4,5-dihydro-3H,1'H-[1,4']biimidazolyl-2-one (6 mg, 11.3%) as yellow solid. MS: m/z=353.3 (M+H+)

Example 9

1-(2-((4,8-dimethylquinazolin-2-yl)ethynyl)-1-methyl-1H-imidazol-4-yl)pyrrolidin-2-one

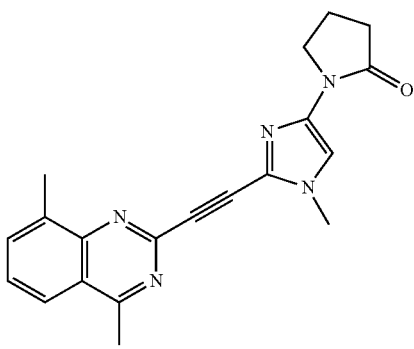 [SMILES: Cc1nc(C#Cc2nc(N3CCCC3=O)cn2C)nc2c(C)cccc12]

a) 4-Bromo-2-ethynyl-1-methyl-1H-imidazole

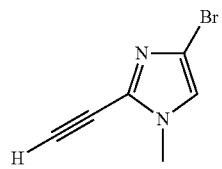

To a stirred mixture of 4-bromo-1-methyl-1H-imidazole-2-carbaldehyde (400 mg, 2.12 mmol, Eq: 1.00) and potassium carbonate (585 mg, 4.23 mmol, Eq: 2) at r.t. in methanol (30.0 ml) under an argon atmosphere was added dimethyl 1-diazo-2-oxopropylphosphonate (488 mg, 381 µl, 2.54 mmol, Eq: 1.2) in one portion. Stirring at r.t. was then continued overnight. The mixture was diluted with Et2O and washed with 5% aq. KHCO3. The aqueous phase was back extracted with Et2O and dried over magnesium sulfate, filtered and concentrated to leave the crude product as light brown oil. The crude material was applied on silica gel and purified by column chromatography using heptane/ethyl acetate (0-50% ethyl acetate) as eluent affording 4-Bromo-2-ethynyl-1-methyl-1H-imidazole (319 mg, 81.5%) as brown solid. MS: m/z=185.0 (M+H+)

b) 4,8-Dimethyl-2-(2-methyl-5-pyrrolidin-1-yl-2H-[1,2,4]triazol-3-ylethynyl)-quinazoline

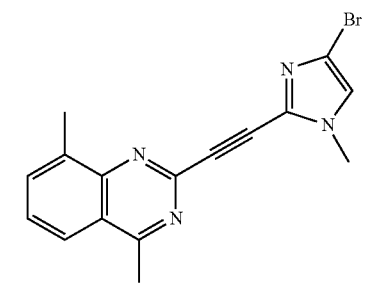 [SMILES: Cc1nc(C#Cc2nc(Br)cn2C)nc2c(C)cccc12]

To a stirred solution of 2-chloro-4,8-dimethylquinazoline (prepared as described in WO2013/50527) (100 mg, 519 µmol, Eq: 1.00) and 4-bromo-2-ethynyl-1-methyl-1H-imidazole (106 mg, 571 µmol, Eq: 1.1) at r.t. in DMF (8.00 ml) under an argon atmosphere were added triethylamine (105 mg, 144 µl, 1.04 mmol, Eq: 2), copper (I) iodide (4.94 mg, 26.0 µmol, Eq: 0.05) and bis(triphenylphosphine)palladium (II) chloride (18.2 mg, 26.0 µmol, Eq: 0.05). The mixture was degassed and back-filled with argon before it was heated to 80° C. Stirring at that temperature was continued over weekend (dark sol.). LCMS showed product peak. The crude material was applied on silica gel and purified by column chromatography using heptane/ethyl acetate (0-100% ethyl acetate) as eluent affording 4,8-Dimethyl-2-(2-methyl-5-pyrrolidin-1-yl-2H[1,2,4]triazol-3-ylethynyl)-quinazoline (55 mg, 31.1%) as light brown solid. MS: m/z=341.1 (M+H+)

c) 1-[2-(4,8-Dimethyl-quinazolin-2-ylethynyl)-1-methyl-1H-imidazol-4-yl]-pyrrolidin-2-one

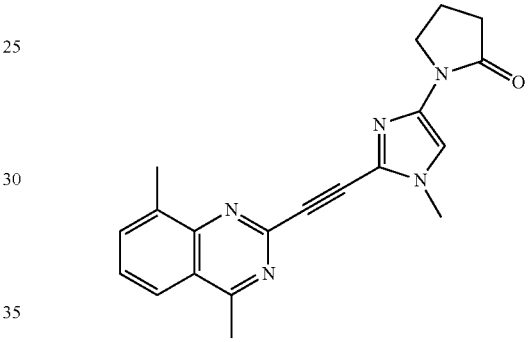

Was prepared in the same manner as described in Example 1d) using 2-((4-bromo-1-methyl-1H-imidazol-2-yl)ethynyl)-4,8-dimethylquinazoline (80 mg, 234 µmol, Eq: 1.00) and pyrrolidin-2-one (39.9 mg, 36.0 µl, 469 µmol, Eq: 2) as starting material, affording 1-[2-(4,8-Dimethyl-quinazolin-2-ylethynyl)-1-methyl-1H-imidazol-4-yl]-pyrrolidin-2-one (2.42 mg, 2.99%) as light yellow solid. MS: m/z=346.2 (M+H+).

Example 10

1-{2-[(E)-2-{4,7-dimethyl-[1,2,4]triazolo[1,5-a]pyrazin-2-yl}ethenyl]-1-methyl-1H-imidazol-4-yl}pyrrolidin-2-one

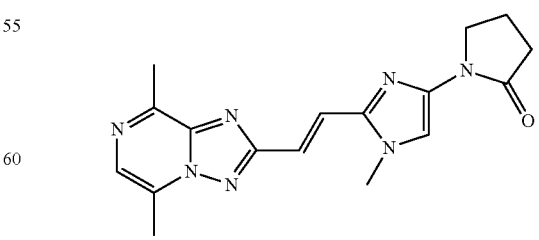

To a solution of 4-bromo-2-[(E)-2-{4,7-dimethyl-[1,2,4]triazolo[1,5-a]pyrazin-2-yl}ethenyl]-1-methyl-1H-imidazole (200 mg, 0.60 mmol) in 1,4-dioxane (10 ml) at 25° C.

in a sealed tube were added pyrrolidin-2-one (0.07 ml, 0.90 mmol), Brettphos palladacycle (71.9 mg, 0.09 mmol) and Ruphos (56 mg, 0.12 mmol) and the mixture was purged with argon for 10 min. After that NaOtBu (173 mg, 1.80 mmol) was added and again purged with argon for another 10 min. The reaction mixture was then heated to 110° C. and stirred at this temperature for 6 h. The reaction mixture was allowed to 25° C., filtered through bed of celite, washed with EtOAc (30 ml). The filtrate was diluted with water (30 ml) and extracted with EtOAc (2×50 ml) and the combined organic layers were washed with water (50 ml), brine (50 ml), dried over Na2SO4 and concentrated in vacuo. The crude was purified by column chromatography via amine silica gel eluted with 40% ethyl acetate in hexane to get 1-{2-[(E)-2-{4,7-dimethyl-[1,2,4]triazolo[1,5-a]pyrazin-2-yl}ethenyl]-1-methyl-1H-imidazol-4-yl}pyrrolidin-2-one (as a yellow solid (60 mg, 29%). MS: M/Z=338.2 (M+H+).

Example 11

1-[2-(2-{4,7-Dimethyl-[1,2,4]triazolo[1,5-a]pyrazin-2-yl}ethyl)-1-methyl-1H-imidazol-4-yl]pyrrolidin-2-one

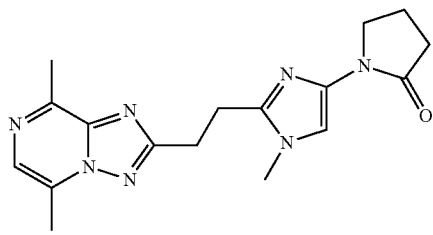 [SMILES: Cc1ncc(C)n2nc(CCc3nc(N4CCCC4=O)cn3C)nc12]

A solution of 1-{2-[(E)-2-{4,7-dimethyl-[1,2,4]triazolo[1,5-a]pyrazin-2-yl}ethenyl]-1-methyl-1H-imidazol-4-yl}pyrrolidin-2-one (60 mg, 0.18 mmol) in methanol (5 ml) was then added raney nickel (30 mg). The reaction mass was stirred under hydrogen balloon pressure for 16 h. After completion of reaction, the reaction mixture was filtered through celite bed, washed with methanol (15 ml) and the filtrate was concentrated under reduced pressure. The crude was purified by silica column using 4% methanol in dichloromethane to give 1-[2-(2-{4,7-dimethyl-[1,2,4]triazolo[1,5-a]pyrazin-2-yl}ethyl)-1-methyl-1H-imidazol-4-yl]pyrrolidin-2-one (16 mg, 26%) as white solid. MS: M/Z=340.2 (M+H+).

Example 12

1-[1-(Cyclopropylmethyl)-2-(2-{4,7-dimethyl-[1,2,4]triazolo[1,5-a]pyrazin-2-yl}ethyl)-1H-imidazol-4-yl]pyrrolidin-2-one

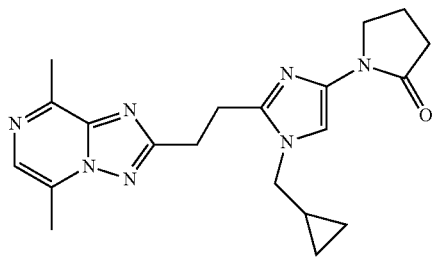 [SMILES: Cc1ncc(C)n2nc(CCc3nc(N4CCCC4=O)cn3CC3CC3)nc12]

a: 1-[1-(Cyclopropylmethyl)-2-[(E)-2-{4,7-dimethyl-[1,2,4]triazolo[1,5-a]pyrazin-2-yl}ethenyl]-1H-imidazol-4-yl]pyrrolidin-2-one

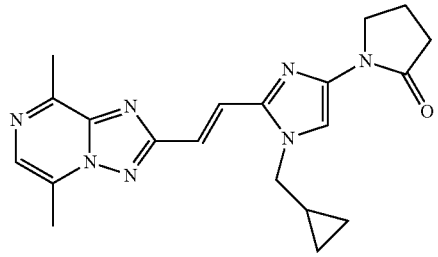 [SMILES: Cc1ncc(C)n2nc(/C=C/c3nc(N4CCCC4=O)cn3CC3CC3)nc12]

Was prepared in the same manner as described in Example 10 using 4-bromo-1-(cyclopropylmethyl)-2-[(E)-2-{4,7-dimethyl-[1,2,4]triazolo[1,5-a]pyrazin-2-yl}ethenyl]-1H-imidazole (170 mg, 0.45 mmol) and pyrrolidin-2-one (0.07 ml, 0.91 mmol) as starting materials, affording 1-[1-(Cyclopropylmethyl)-2-[(E)-2-{4,7-dimethyl-[1,2,4]triazolo[1,5-a]pyrazin-2-yl}ethenyl]-1H-imidazol-4-yl]pyrrolidin-2-one (70 mg, 40%) as yellow solid; MS: M/Z=378 (M+H+).

b: 1-[1-(Cyclopropylmethyl)-2-(2-{4,7-dimethyl-[1,2,4]triazolo[1,5-a]pyrazin-2-yl}ethyl)-1H-imidazol-4-yl]pyrrolidin-2-one

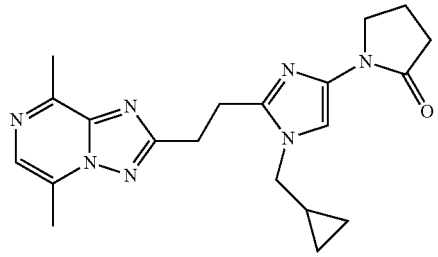 [SMILES: Cc1ncc(C)n2nc(CCc3nc(N4CCCC4=O)cn3CC3CC3)nc12]

Was prepared in the same manner as described in Example 11 using 1-[1-(Cyclopropylmethyl)-2-[(E)-2-{4,7-dimethyl-[1,2,4]triazolo[1,5-a]pyrazin-2-yl}ethenyl]-1H-imidazol-4-yl]pyrrolidin-2-one (70 mg, 0.186 mmol) as starting material, affording 1-[1-(Cyclopropylmethyl)-2-(2-{4,7-dimethyl-[1,2,4]triazolo[1,5-a]pyrazin-2-yl}ethyl)-1H-imidazol-4-yl]pyrrolidin-2-one (7 mg, 11%) as white solid; MS: M/Z=380.1 (M+H+).

Example 13

1-[2-(2-{4,7-Dimethyl-[1,2,4]triazolo[1,5-a]pyrazin-2-yl}ethyl)-1-(2,2,2-trifluoroethyl)-1H-imidazol-4-yl]pyrrolidin-2-one

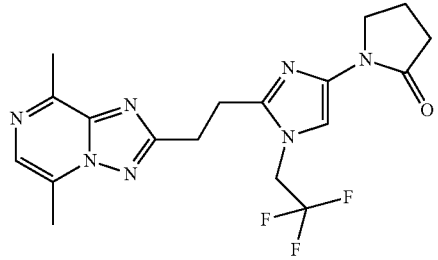 [SMILES: Cc1ncc(C)n2nc(CCc3nc(N4CCCC4=O)cn3CC(F)(F)F)nc12]

a: 4-Bromo-1-(triphenylmethyl)-1H-imidazole

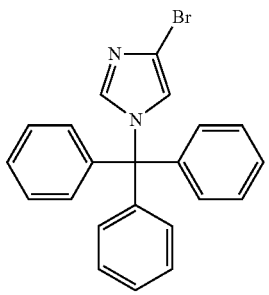 [SMILES: Brc1cn(C(c2ccccc2)(c2ccccc2)c2ccccc2)cn1]

A solution of 4-bromo-1H-imidazole (10 g, 68.04 mmol) in THF (330 ml) was cooled to 0° C. K2CO3 (18.77 g, 136.08 mmol) was added slowly at 0° C. After stirring for 1 h at 0° C., iodomethane (8.50 ml, 136.08 mmol) was added drop wise at 0° C. The mixture was allowed to 25° C. and stirred for 16 h at 25° C. The reaction mass was diluted with water (100 ml) and extracted with ethyl acetate (3×250 ml). The organic layer was washed with water (2×100 ml), brine (100 ml) and dried over sodium sulfate, filtered and evaporated. The crude was purified by silica column chromatography eluted with 10% ethyl acetate in hexane to give 4-bromo-1-(triphenylmethyl)-1H-imidazole (12 g, 50%) as a colorless liquid.

b: 4-Bromo-1-(triphenylmethyl)-1H-imidazole-2-carbaldehyde

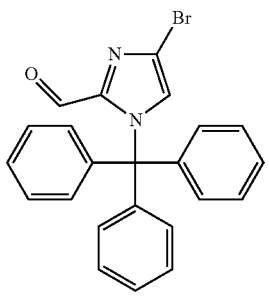 [SMILES: O=Cc1nc(Br)cn1C(c1ccccc1)(c1ccccc1)c1ccccc1]

To a solution of 4-Bromo-1-(triphenylmethyl)-1H-imidazole (6 g, 15.42 mmol) in tetrahydrofuran (250 ml) at −78° C. under argon was added drop wise n-butyl lithium (1.6M in hexane, 12.44 ml, 18.55 mmol). The resulting mixture was stirred for 30 minutes at −78° C. Then dimethylformamide (2.49 ml, 30.89 mmol) dissolving in 45 ml of THF was added drop wise at −78° C. and the mixture was allowed to 25° C. slowly. The mixture was quenched with saturated ammonium chloride solution (500 ml) at 25° C. and extracted with ethyl acetate (2×500 ml), the separated organic layers were washed with water (2×400 ml) and brine (400 ml), dried over sodium sulfate, filtered and evaporated. Crude was purified by normal silica gel column eluted with 30% ethyl acetate in hexane to give 4-Bromo-1-(triphenylmethyl)-1H-imidazole-2-carbaldehyde (2 g, 31%) as white solid c: 4-Bromo-1H-imidazole-2-carbaldehyde

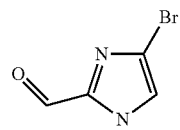

To a solution of 4-bromo-1-(triphenylmethyl)-1H-imidazole-2-carbaldehyde (5.5 g, 13.18 mmol) in methanol (100 ml) was added AcOH (1.5 ml, 26.4 mmol), then it was allowed to 60° C. and stirred at this temperature for 2 h. After completion of reaction, the reaction mixture was allowed to 25° C. and concentrated under reduced pressure. The crude residue was diluted with water (150 ml), neutralized with bi carbonate solution adjust pH-7 and extracted with ethyl acetate (2×300 ml), separated the organic layer and washed with brine (100 ml), and dried over sodium sulfate, filtered and concentrated to get the crude. The crude was purified by combiflash column using 30% ethyl acetate in hexane to get 4-bromo-1H-imidazole-2-carbaldehyde (700 mg, 31%) as brown solid.

d: 4-Bromo-1-(2,2,2-trifluoroethyl)-1H-imidazole-2-carbaldehyde

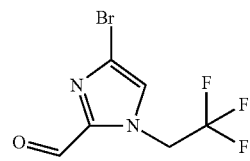 [SMILES: O=Cc1nc(Br)cn1CC(F)(F)F]

A solution of 4-bromo-1H-imidazole-2-carbaldehyde (350 mg, 2 mmol) in DMF (10 ml) was cooled to 0° C. Cs2CO3 (1.71 g, 2 mmol) was added slowly at 0° C. After stirring for 10 min at 0° C., 2, 2-difluoroethyl trifluoromethanesulfonate (928 ng, 2 mmol) was added drop wise at 0° C. The mixture was allowed to 25° C. and stirred for 2 h at same temperature. The reaction mass was diluted with water (50 ml) and extracted with ethyl acetate (3×100 ml). The organic layer was washed with water (2×100 ml), brine (50 ml) and dried over sodium sulfate, filtered and evaporated. The crude was purified by combiflash column chromatography eluted with 20% ethyl acetate in hexane to give 4-Bromo-1-(2,2,2-trifluoroethyl)-1H-imidazole-2-carbaldehyde (350 mg, 68%) as white solid. MS: M/Z=257 (M+H+).

e: 4-Bromo-2-[(E)-2-{4,7-dimethyl-[1,2,4]triazolo[1,5-a]pyrazin-2-yl}ethenyl]-1-(2,2,2-trifluoroethyl)-1H-imidazole

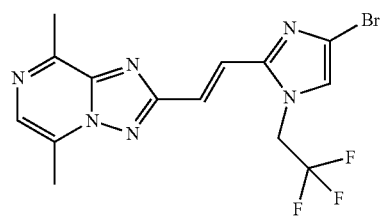 [SMILES: Cc1ncc(C)n2nc(/C=C/c3nc(Br)cn3CC(F)(F)F)nc12]

Was prepared in the same manner as described in Example 1c) using 4-bromo-1-(2,2,2-trifluoroethyl)-1H-imidazole-2-carbaldehyde (4d) (250 mg, 0.97 mmol) and {4,7-dimethyl-[1,2,4]triazolo[1,5-a]pyrazin-2-yl}methyl) triphenylphosphanium chloride (5) (412 mg, 0.97 mmol) as starting material, affording 4-Bromo-2-[(E)-2-{4,7-dimethyl-[1,2,4]triazolo[1,5-a]pyrazin-2-yl}ethenyl]-1-(2,2,2-trifluoroethyl)-1H-imidazole (180 mg, 46%) as white solid; MS: M/Z=401 (M+H+).

f: 1-{2-[(E)-2-{4,7-Dimethyl-[1,2,4]triazolo[1,5-a]pyrazin-2-yl}ethenyl]-1-(2,2,2-trifluoroethyl)-1H-imidazol-4-yl}pyrrolidin-2-one

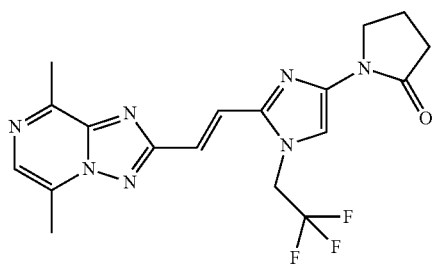 [SMILES: Cc1ncc(C)n2nc(/C=C/c3nc(N4CCCC4=O)cn3CC(F)(F)F)nc12]

To a solution of 4-Bromo-2-[(E)-2-{4,7-dimethyl-[1,2,4]triazolo[1,5-a]pyrazin-2-yl}ethenyl]-1-(2,2,2-trifluoroethyl)-1H-imidazole (6a) (160 mg, 0.4 mmol) in 1,4-dioxane (6 ml) at 25° C. in a sealed tube were added pyrrolidin-2-one (0.06 ml, 0.8 mmol), Brettphos palladacycle (47.93 mg, 0.06 mmol) and Ruphos (37.3 mg, 0.08 mmol) and the mixture was purged with argon for 10 min. After that NaOtBu (115.3 mg, 1.2 mmol) was added and again purged with argon for another 10 min. The reaction mixture was then heated to 110° C. and stirred at this temperature for 6 h. The reaction mixture was allowed to 25° C., filtered through bed of celite, washed with EtOAc (30 ml). The filtrate was diluted with water (30 ml) and extracted with EtOAc (2×50 ml) and the combined organic layers were washed with water (50 ml), brine (50 ml), dried over Na2SO4 and concentrated in vacuo. The crude was purified by column chromatography via amine silica gel eluted with 40% ethyl acetate in hexane to get 1-{2-[(E)-2-{4,7-Dimethyl-[1,2,4]triazolo[1,5-a]pyrazin-2-yl}ethenyl]-1-(2,2,2-trifluoroethyl)-1H-imidazol-4-yl}pyrrolidin-2-one (60 mg, 37%) as yellow solid; MS: M/Z=406 (M+H+).

g: 1-[2-(2-{4,7-Dimethyl-[1,2,4]triazolo[1,5-a]pyrazin-2-yl}ethyl)-1-(2,2,2-trifluoroethyl)-1H-imidazol-4-yl]pyrrolidin-2-one

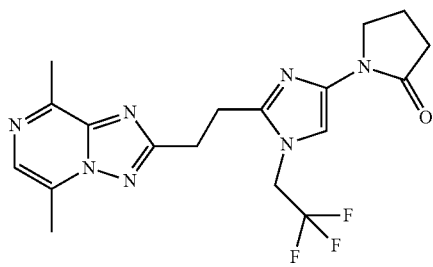 [SMILES: Cc1ncc(C)n2nc(CCc3nc(N4CCCC4=O)cn3CC(F)(F)F)nc12]

A solution of 1-{2-[(E)-2-{4,7-dimethyl-[1,2,4]triazolo[1,5-a]pyrazin-2-yl}ethenyl]-1-(2,2,2-trifluoroethyl)-1H-imidazol-4-yl}pyrrolidin-2-one (8d) (70 mg, 0.17 mmol) in methanol (5 ml) and then added raney nickel (30 mg). The reaction mass was stirred under hydrogen balloon pressure for 16 h. After completion of reaction, the reaction mixture was filtered through celite bed, washed with methanol (15 ml) and the filtrate was concentrated under reduced pressure. The crude was purified by silica column using 4% methanol in dichloromethane to give 1-[2-(2-{4,7-Dimethyl-[1,2,4]triazolo[1,5-a]pyrazin-2-yl}ethyl)-1-(2,2,2-trifluoroethyl)-1H-imidazol-4-yl]pyrrolidin-2-one (20 mg, 28%) as white solid; MS: M/Z=408.2 (M+H+).

Example 14

1-[1-(2,2-difluoroethyl)-2-(2-{4,7-dimethyl-[1,2,4]triazolo[1,5-a]pyrazin-2-yl}ethyl)-1H-imidazol-4-yl]pyrrolidin-2-one

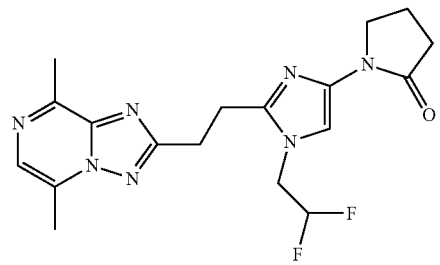

a: 4-Bromo-1-(2,2-difluoroethyl)-1H-imidazole-2-carbaldehyde

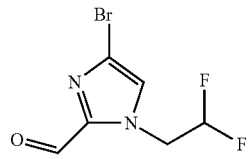 [SMILES: O=Cc1nc(Br)cn1CC(F)F]

A solution of 4-bromo-1H-imidazole-2-carbaldehyde (450 mg, 2.57 mmol) in DMF (12 ml) was cooled to 0° C. Cs2CO3 (1.71 g, 5.14 mmol) was added slowly at 0° C. After stirring for 10 min at 0° C., 2, 2-difluoroethyl trifluoromethanesulfonate (825.5 mg, 3.87 mmol) was added drop wise at 0° C. The mixture was allowed to 25° C. and stirred for 2 h at same temperature. The reaction mass was diluted with water (50 ml) and extracted with ethyl acetate (3×100 ml). The organic layer was washed with water (2×100 ml), brine (50 ml) and dried over sodium sulfate, filtered and evaporated. The crude was purified by combiflash column chromatography eluted with 20% ethyl acetate in hexane to give 4-bromo-1-(2,2-difluoroethyl)-1H-imidazole-2-carbaldehyde (220 mg, 36%) as a colorless liquid; MS: M/Z=239 (M+H+).

b: 4-Bromo-1-(2,2-difluoroethyl)-2-[(E)-2-{4,7-dimethyl-[1,2,4]triazolo[1,5-a]pyrazin-2-yl}ethenyl]-1H-imidazole

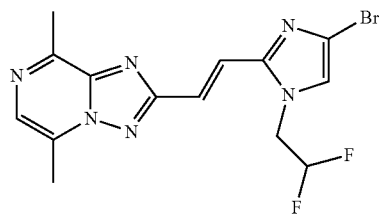 [SMILES: Cc1ncc(C)n2nc(/C=C/c3nc(Br)cn3CC(F)F)nc12]

Was prepared in the same manner as described in Example 5a using 4-bromo-1-(2,2-difluoroethyl)-1H-imidazole-2-carbaldehyde (200 mg, 0.84 mmol) and {4,7-dimethyl-[1,2,4]triazolo[1,5-a]pyrazin-2-yl}methyl)triphenylphosphanium chloride (354 mg, 0.84 mmol) as starting materials, affording 4-Bromo-1-(2,2-difluoroethyl)-2-[(E)-2-{4,7-dimethyl-[1,2,4]triazolo[1,5-a]pyrazin-2-yl}ethenyl]-1H-imidazole (120 mg, 38%) as white solid; MS: M/Z=383 (M+H+).

c: 1-[1-(2,2-difluoroethyl)-2-[(E)-2-{4,7-dimethyl-[1,2,4]triazolo[1,5-a]pyrazin-2-yl}ethenyl]-1H-imidazol-4-yl]pyrrolidin-2-one

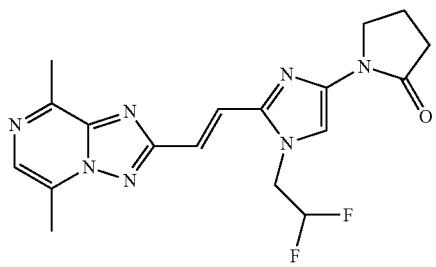

Was prepared in the same manner as described in Example 10 using 4-bromo-1-(2,2-difluoroethyl)-2-[(E)-2-{4,7-dimethyl-[1,2,4]triazolo[1,5-a]pyrazin-2-yl}ethenyl]-1H-imidazole (100 mg, 0.26 mmol) and pyrrolidin-2-one (0.04 ml, 0.91 mmol) as starting materials, affording 1-[1-(2,2-difluoroethyl)-2-[(E)-2-{4,7-dimethyl-[1,2,4]triazolo[1,5-a]pyrazin-2-yl}ethenyl]-1H-imidazol-4-yl]pyrrolidin-2-one (13 mg, 12%) as white solid; MS: M/Z=388.2 (M+H+).

d: 1-[1-(2,2-difluoroethyl)-2-(2-{4,7-dimethyl-[1,2,4]triazolo[1,5-a]pyrazin-2-yl}ethyl)-1H-imidazol-4-yl]pyrrolidin-2-one

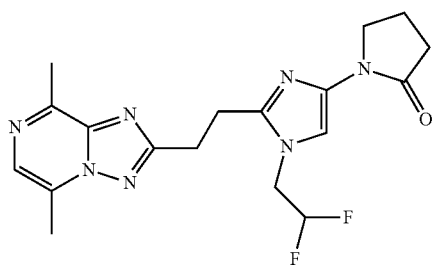

Was prepared in the same manner as described in Example 11 using 1-[1-(2,2-difluoroethyl)-2-[(E)-2-{4,7-dimethyl-[1,2,4]triazolo[1,5-a]pyrazin-2-yl}ethenyl]-1H-imidazol-4-yl]pyrrolidin-2-one (23 mg, 0.06 mmol) as starting material, affording 1-[1-(2,2-difluoroethyl)-2-(2-{4,7-dimethyl-[1,2,4]triazolo[1,5-a]pyrazin-2-yl}ethyl)-1H-imidazol-4-yl]pyrrolidin-2-one (6 mg, 25%) as white solid; MS: M/Z=390.4 (M+H+).

Example 15

1-[2-(2-{4,7-Dimethyl-[1,2,4]triazolo[1,5-a]pyrazin-2-yl}ethynyl)-1-methyl-1H-imidazol-4-yl]pyrrolidin-2-one

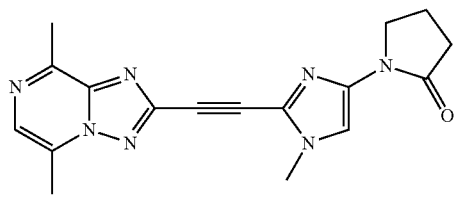 [SMILES: Cc1ncc(C)n2nc(C#Cc3nc(N4CCCC4=O)cn3C)nc12]

a: 1-Methyl-4-(2-oxopyrrolidin-1-yl)-1H-imidazole-2-carbaldehyde

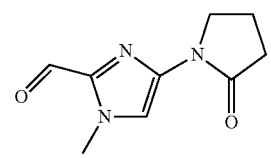

To a solution of 4-bromo-1-methyl-1H-imidazole-2-carbaldehyde (400 mg, 5.8 mmol) and pyrrolidin-2-one (0.35 ml, 2.1 mmol) in toluene (20 ml) was added Cs2CO3 (3.7 g, 11.6 mmol), xantphos (335 mg, 0.58 mmol) and the mixture was purged with argon for 10 min. Pd2(dba)3 (1.03 g, 3.17 mmol) was added and purged with argon for another 10 min. The reaction mixture was then heated to 50° C. and stirred at this temperature for 16 h under argon. After that TLC was checked and starting material was present so added another 0.5 eq xantphos and 0.5 eq Pd2(dba)3 and 1 eq Cs2CO3 continued another 3 h at 90° C. for 3 h. The reaction mixture was allowed to 25° C., filtered through bed of celite, concentrated in vacuo. The crude was purified by column chromatography via silica (100-200 mesh) eluted with 20% ethyl acetate in hexane to get 1-methyl-4-(2-oxopyrrolidin-1-yl)-1H-imidazole-2-carbaldehyde (60 mg, 15%) as a yellow solid. MS: M/Z=194 (M+H+).

b: 1-(2-Ethynyl-1-methyl-1H-imidazol-4-yl) pyrrolidin-2-one

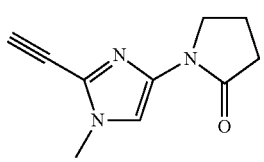

To a solution of 1-methyl-4-(2-oxopyrrolidin-1-yl)-1H-imidazole-2-carbaldehyde (60 mg, 0.311 mmol) in methanol (6 ml) under argon at 25° C. was added Bestmann ohira reagent (72 mg, 0.373 mmol) and K2CO3 (85 g, 0.622 mmol) and the mixture was stirred at 25° C. for 2 h. After that TLC was checked and filtered through bed of celite and concentrated in vacuo. The crude was purified by combiflash column chromatography eluted with 20% ethyl acetate in hexane to get 1-(2-ethynyl-1-methyl-1H-imidazol-4-yl) pyrrolidin-2-one as a white solid (30 mg, 51%). MS: M/Z=190 (M+H+).

c: 1-[2-(2-{4,7-Dimethyl-[1,2,4]triazolo[1,5-a]pyrazin-2-yl}ethynyl)-1-methyl-1H-imidazol-4-yl] pyrrolidin-2-one

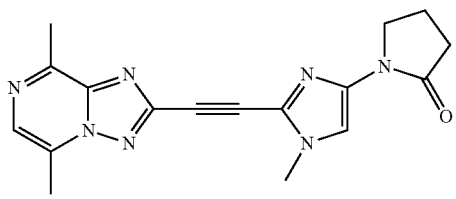

To a solution of 1-(2-ethynyl-1-methyl-1H-imidazol-4-yl) pyrrolidin-2-one (55 mg, 0.291 mmol) and 2-bromo-4,7-dimethyl-[1,2,4]triazolo[1,5-a]pyrazine (73 mg, 0.32 mmol) in DMF (3 ml) was added TEA (0.08 ml, 0.58 mmol) followed by CuI and the mixture was purged with argon for 10 min. After that Pd(PPh3)2Cl2 (11 mg, 0.015 mmol) was added and purged with argon for another 5 min. The reaction mixture was then heated to 75° C. and stirred at this temperature for 2 h under argon. After that filtrate the reaction mixture via a bed of celite, diluted with water (30 ml) extracted with EtOAc (2×50 ml) and the combined organic layers were washed with water (50 ml), brine (50 ml), dried over Na2SO4 and concentrated in vacuo. The crude was purified by prep TLC to get 1-[2-(2-{4,7-dimethyl-[1,2,4]triazolo[1,5-a]pyrazin-2-yl}ethynyl)-1-methyl-1H-imidazol-4-yl]pyrrolidin-2-one (21) as a white sticky solid (4 mg, 4%). MS: M/Z=336 (M+H+).

Example 16

1-[1-(Cyclopropylmethyl)-2-(2-{5,8-dimethyl-[1,2,4]triazolo[1,5-c]pyrimidin-2-yl}ethyl)-1H-imidazol-4-yl]pyrrolidin-2-one

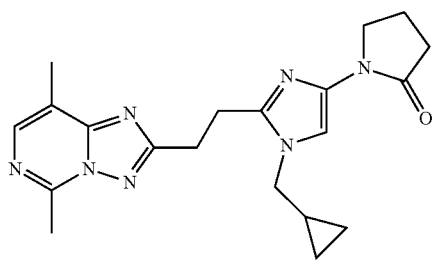 [SMILES: Cc1cnc(C)n2nc(CCc3nc(N4CCCC4=O)cn3CC3CC3)nc12]

a: 4-Bromo-1-(cyclopropylmethyl)-2-[(E)-2-{5,8-dimethyl-[1,2,4]triazolo[1,5-c]pyrimidin-2-yl}ethenyl]-1H-imidazol

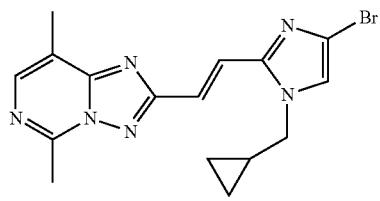 [SMILES: Cc1cnc(C)n2nc(/C=C/c3nc(Br)cn3CC3CC3)nc12]

Was prepared in the same manner as described in Example 1c using 4-bromo-1-(cyclopropylmethyl)-1H-imidazole-2-carbaldehyde (400 mg, 1.74 mmol) and {5,8-dimethyl-[1,2,4]triazolo[1,5-c]pyrimidin-2-yl}methyl)triphenylphosphanium chloride (740 mg, 1.74 mmol) as starting material, affording 4-Bromo-1-(cyclopropylmethyl)-2-[(E)-2-{5,8-dimethyl-[1,2,4]triazolo[1,5-c]pyrimidin-2-yl}ethenyl]-1H-imidazol (360 mg, 55%) as off white solid. MS: M/Z=372.8 (M+H+).

b: 1-[1-(Cyclopropylmethyl)-2-[(E)-2-{5, 8-dimethyl-[1, 2, 4]triazolo[1,5-c]pyrimidin-2-yl}ethenyl]-1H-imidazol-4-yl]pyrrolidin-2-one

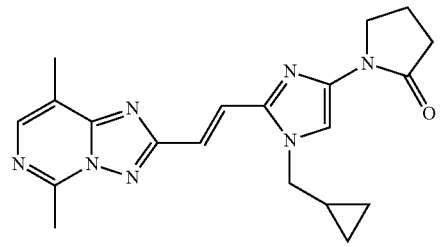 [SMILES: Cc1cnc(C)n2nc(/C=C/c3nc(N4CCCC4=O)cn3CC3CC3)nc12]

Was prepared in the same manner as described in Example 1d using 4-bromo-1-(cyclopropylmethyl)-2-[(E)-2-{5,8-dimethyl-[1,2,4]triazolo[1,5-c]pyrimidin-2-yl}ethenyl]-1H-imidazol (200 mg, 0.54 mmol) and pyrrolidin-2-one (0.08 ml, 0.90 mmol) as starting materials, affording 1-[1-(Cyclopropylmethyl)-2-[(E)-2-{5, 8-dimethyl-[1, 2, 4]triazolo[1,5-c]pyrimidin-2-yl}ethenyl]-1H-imidazol-4-yl]pyrrolidin-2-one (90 mg, 45%) as off white solid. MS: M/Z=378.0 (M+H+).

c: 1-[1-(Cyclopropylmethyl)-2-(2-{5,8-dimethyl-[1,2,4]triazolo[1,5-c]pyrimidin-2-yl}ethyl)-1H-imidazol-4-yl]pyrrolidin-2-one

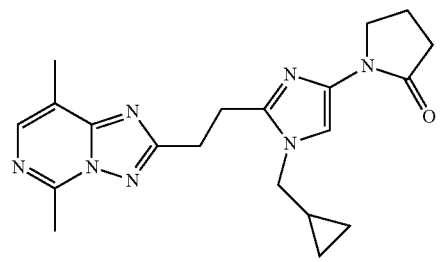 [SMILES: Cc1cnc(C)n2nc(CCc3nc(N4CCCC4=O)cn3CC3CC3)nc12]

Was prepared in the same manner as described in Example 11 using 1-[1-(cyclopropylmethyl)-2-[(E)-2-{5,8-dimethyl-[1,2,4]triazolo[1,5-c]pyrimidin-2-yl}ethenyl]-1H-imidazol-4-yl]pyrrolidin-2-one (90 mg, 0.239 mmol) as starting material, affording 1-[1-(Cyclopropylmethyl)-2-(2-{5,8-dimethyl-[1,2,4]triazolo[1,5-c]pyrimidin-2-yl}ethyl)-1H-imidazol-4-yl]pyrrolidin-2-one (26 mg, 29%) as white solid. MS: M/Z=380.2 (M+H+).

Example 17

1-[2-[2-(5,8-dimethyl-[1,2,4]triazolo[1,5-c]pyrimidin-2-yl)ethyl]-1-phenyl-imidazol-4-yl]pyrrolidin-2-one a: 2-[(E)-2-(4-bromo-1-phenyl-imidazol-2-yl)vinyl]-5,8-dimethyl-[1,2,4]triazolo[1,5-c]pyrimidine

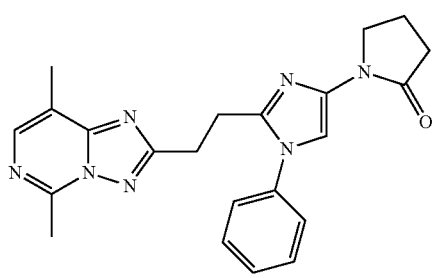 [SMILES: Cc1cnc(C)n2nc(CCc3nc(N4CCCC4=O)cn3-c3ccccc3)nc12]

Was prepared in the same manner as described in Example 1c using 4-bromo-1-phenyl-1H-imidazole (200 mg, 0.80 mmol) and {5,8-dimethyl-[1,2,4]triazolo[1,5-c]pyrimidin-2-yl}methyl)triphenylphosphanium chloride (338 mg, 0.80 mmol) as starting material, affording 2-[(E)-2-(4-bromo-1-phenyl-imidazol-2-yl)vinyl]-5,8-dimethyl-[1,2,4]triazolo[1,5-c]pyrimidine (180 mg, 58%) as off white solid; MS: M/Z=395 (M+H+).

b: 2-[(E)-2-(4-bromo-1-phenyl-imidazol-2-yl)vinyl]-5,8-dimethyl-[1,2,4]triazolo[1,5-c]pyrimidine

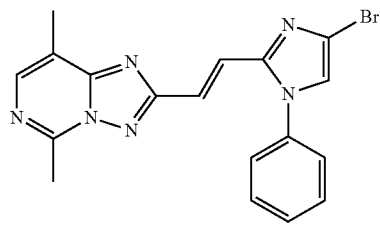 [SMILES: Cc1cnc(C)n2nc(/C=C/c3nc(Br)cn3-c3ccccc3)nc12]

Was prepared in the same manner as described in Example 1d using 2-[(E)-2-(4-bromo-1-phenyl-imidazol-2-yl)vinyl]-5,8-dimethyl-[1,2,4]triazolo[1,5-c]pyrimidine (110 mg, 0.28 mmol) and pyrrolidin-2-one (0.045 ml, 0.91 mmol) as starting materials, affording 2-[(E)-2-(4-bromo-1-phenyl-imidazol-2-yl)vinyl]-5,8-dimethyl-[1,2,4]triazolo[1,5-c]pyrimidine (55 mg, 50%) as white solid; MS: M/Z=399 (M+H+).

c: 1-[2-[2-(5,8-dimethyl-[1,2,4]triazolo[1,5-c]pyrimidin-2-yl)ethyl]-1-phenyl-imidazol-4-yl]pyrrolidin-2-one

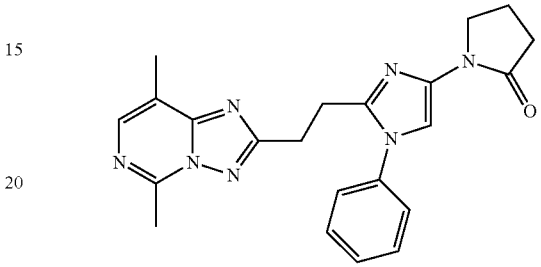

Was prepared in the same manner as described in Example 11 using 2-[(E)-2-(4-bromo-1-phenyl-imidazol-2-yl)vinyl]-5,8-dimethyl-[1,2,4]triazolo[1,5-c]pyrimidine (15 mg, 0.04 mmol) as starting material, affording 1-[2-[2-(5,8-dimethyl-[1,2,4]triazolo[1,5-c]pyrimidin-2-yl)ethyl]-1-phenyl-imidazol-4-yl]pyrrolidin-2-one (4 mg, 25%) as off white solid; MS: M/Z=402 (M+H+).

Example 18

1-[2-(2-{5,8-dimethyl-[1,2,4]triazolo[1,5-c]pyrimidin-2-yl}ethyl)-1-(2,2,2-trifluoroethyl)-1H-imidazol-4-yl]pyrrolidin-2-one

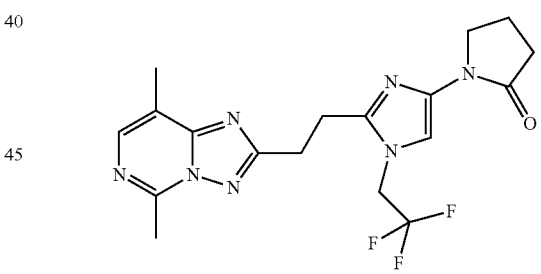

a: 4-Bromo-2-[(E)-2-{5,8-dimethyl-[1,2,4]triazolo[1,5-c]pyrimidin-2-yl}ethenyl]-1-(2,2,2-trifluoroethyl)-1H-imidazole

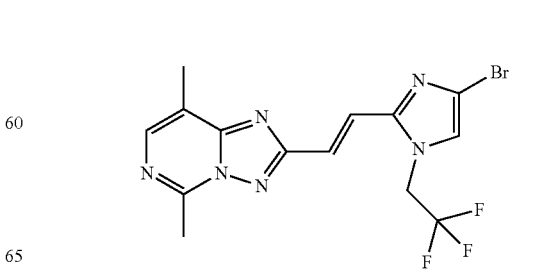

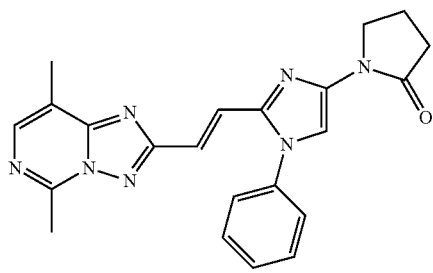 [SMILES: Cc1cnc(C)n2nc(/C=C/c3nc(N4CCCC4=O)cn3-c3ccccc3)nc12]

Was prepared in the same manner as described in Example 1c using 4-bromo-1-(2,2,2-trifluoroethyl)-1H-imidazole-2-carbaldehyde (250 mg, 0.97 mmol) and {5,8-dimethyl-[1,2,4]triazolo[1,5-c]pyrimidin-2-yl}methyl)triphenylphosphanium chloride (412 mg, 0.97 mmol) as starting material, affording 4-Bromo-2-[(E)-2-{5,8-dimethyl-[1,2,4]triazolo[1,5-c]pyrimidin-2-yl}ethenyl]-1-(2,2,2-trifluoroethyl)-1H-imidazole (170 mg, 43%) as white solid; MS: M/Z=401 (M+H+).

b: 1-{2-[(E)-2-{5,8-Dimethyl-[1,2,4]triazolo[1,5-c]pyrimidin-2-yl}ethenyl]-1-(2,2,2-trifluoroethyl)-1H-imidazol-4-yl}pyrrolidin-2-one

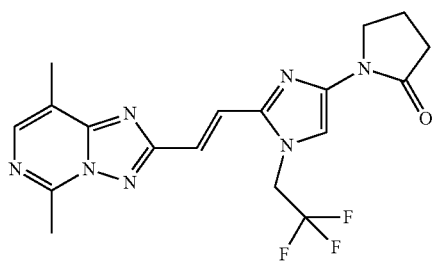 [SMILES: Cc1cnc(C)n2nc(/C=C/c3nc(N4CCCC4=O)cn3CC(F)(F)F)nc12]

Was prepared in the same manner as described in Example 1d using 4-bromo-2-[(E)-2-{5,8-dimethyl-[1,2,4]triazolo[1,5-c]pyrimidin-2-yl}ethenyl]-1-(2,2,2-trifluoroethyl)-1H-imidazole (170 mg, 0.42 mmol) and pyrrolidin-2-one (0.065 ml, 0.85 mmol) as starting materials, affording 1-{2-[(E)-2-{5,8-Dimethyl-[1,2,4]triazolo[1,5-c]pyrimidin-2-yl}ethenyl]-1-(2,2,2-trifluoroethyl)-1H-imidazol-4-yl}pyrrolidin-2-one (70 mg, 41%) as yellow solid; MS: M/Z=406 (M+H+).

c: 1-[2-(2-{5,8-dimethyl-[1,2,4]triazolo[1,5-c]pyrimidin-2-yl}ethyl)-1-(2,2,2-trifluoroethyl)-1H-imidazol-4-yl]pyrrolidin-2-one

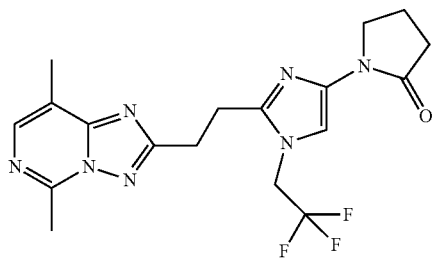 [SMILES: Cc1cnc(C)n2nc(CCc3nc(N4CCCC4=O)cn3CC(F)(F)F)nc12]

Was prepared in the same manner as described in Example 11 using 1-{2-[(E)-2-{5,8-Dimethyl-[1,2,4]triazolo[1,5-c]pyrimidin-2-yl}ethenyl]-1-(2,2,2-trifluoroethyl)-1H-imidazol-4-yl}pyrrolidin-2-one (8d) (70 mg, 0.17 mmol) as starting material, affording 1-[2-(2-{5,8-dimethyl-[1,2,4]triazolo[1,5-c]pyrimidin-2-yl}ethyl)-1-(2,2,2-trifluoroethyl)-1H-imidazol-4-yl]pyrrolidin-2-one (15 mg, 21%) as off white solid; MS: M/Z=408.2 (M+H+).

Example 19

1-[1-(2,2-difluoroethyl)-2-(2-{5,8-dimethyl-[1,2,4]triazolo[1,5-c]pyrimidin-2-yl}ethyl)-1H-imidazol-4-yl]pyrrolidin-2-one

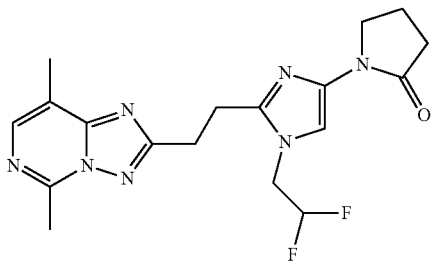 [SMILES: Cc1cnc(C)n2nc(CCc3nc(N4CCCC4=O)cn3CC(F)F)nc12]

a: 4-Bromo-1-(2,2-difluoroethyl)-2-[(E)-2-{5,8-dimethyl-[1,2,4]triazolo[1,5-c]pyrimidin-2-yl}ethenyl]-1H-imidazole

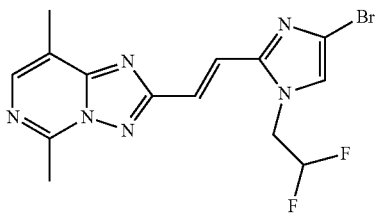 [SMILES: Cc1cnc(C)n2nc(/C=C/c3nc(Br)cn3CC(F)F)nc12]

Was prepared in the same manner as described in Example 1c using 4-bromo-1-(2,2-difluoroethyl)-1H-imidazole-2-carbaldehyde (200 mg, 0.84 mmol) and {5,8-dimethyl-[1,2,4]triazolo[1,5-c]pyrimidin-2-yl}methyl)triphenylphosphanium chloride (354 mg, 0.84 mmol) as starting material, affording 4-Bromo-1-(2,2-difluoroethyl)-2-[(E)-2-{5,8-dimethyl-[1,2,4]triazolo[1,5-c]pyrimidin-2-yl}ethenyl]-1H-imidazole (125 mg, 38%) as off white solid; MS: M/Z=385 (M+H+).

b: 1-[1-(2,2-difluoroethyl)-2-[(E)-2-{5,8-dimethyl-[1,2,4]triazolo[1,5-c]pyrimidin-2-yl}ethenyl]-1H-imidazol-4-yl]pyrrolidin-2-one

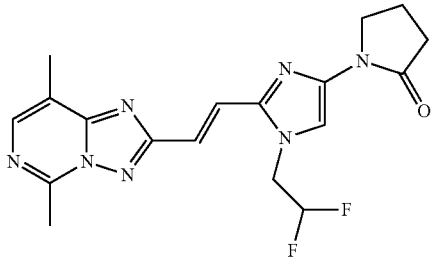 [SMILES: Cc1cnc(C)n2nc(/C=C/c3nc(N4CCCC4=O)cn3CC(F)F)nc12]

Was prepared in the same manner as described in Example 10 using 4-bromo-1-(2, 2-difluoroethyl)-2-[(E)-2-{5, 8-dimethyl-[1, 2, 4]triazolo[1,5-c]pyrimidin-2-yl}ethenyl]-1H-imidazole (150 mg, 0.40 mmol) and pyrrolidin-2-one (0.06 ml, 0.80 mmol) as starting materials, affording 1-[1-(2,2-difluoroethyl)-2-[(E)-2-{5,8-dimethyl-[1,2,4]triazolo[1,5-c]pyrimidin-2-yl}ethenyl]-1H-imidazol-4-yl]pyrrolidin-2-one (70 mg, 41%) as yellow solid; MS: M/Z=406 (M+H+).

c: 1-[1-(2,2-difluoroethyl)-2-(2-{5,8-dimethyl-[1,2,4]triazolo[1,5-c]pyrimidin-2-yl}ethyl)-1H-imidazol-4-yl]pyrrolidin-2-one

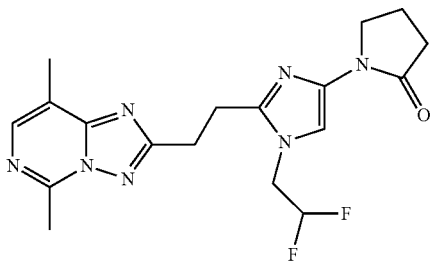 [SMILES: Cc1cnc(C)n2nc(CCc3nc(N4CCCC4=O)cn3CC(F)F)nc12]

Was prepared in the same manner as described in Example 11 using 1-[1-(2,2-difluoroethyl)-2-[(E)-2-{5,8-dimethyl-[1,2,4]triazolo[1,5-c]pyrimidin-2-yl}ethenyl]-1H-imidazol-4-yl]pyrrolidin-2-one (30 mg, 0.08 mmol) as starting material, affording 1-[1-(2,2-difluoroethyl)-2-(2-{5,8-dimethyl-[1,2,4]triazolo[1,5-c]pyrimidin-2-yl}ethyl)-1H-imidazol-4-yl]pyrrolidin-2-one (11 mg, 37%) as white solid; MS: M/Z=390.0 (M+H+).

Example 20

1-{2-[(E)-2-{4,7-Dimethyl-[1,2,4]triazolo[1,5-a]pyrazin-2-yl}ethenyl]-1-phenyl-1H-imidazol-4-yl}pyrrolidin-2-one

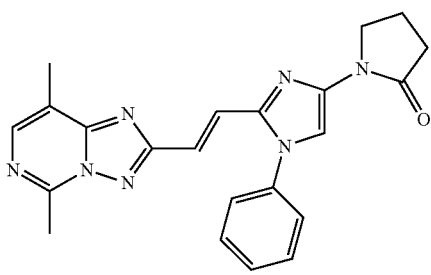 [SMILES: Cc1cnc(C)n2nc(/C=C/c3nc(N4CCCC4=O)cn3-c3ccccc3)nc12]

Was prepared in the same manner as described in Example 1d using 4-bromo-2-[(E)-2-{4,7-dimethyl-[1,2,4]triazolo[1,5-a]pyrazin-2-yl}ethenyl]-1-phenyl-1H-imidazole. (110 mg, 0.28 mmol) and pyrrolidin-2-one (0.045 ml, 0.91 mmol) as starting material, affording 1-{2-[(E)-2-{4,7-Dimethyl-[1,2,4]triazolo[1,5-a]pyrazin-2-yl}ethenyl]-1-phenyl-1H-imidazol-4-yl}pyrrolidin-2-one (55 mg, 50%) as white solid; MS: M/Z=399 (M+H+).

Example 21

1-[2-(2-{5,7-dimethyl-[1,2,4]triazolo[1,5-a]pyrimidin-2-yl}ethyl)-1-methyl-1H-imidazol-4-yl]pyrrolidin-2-one

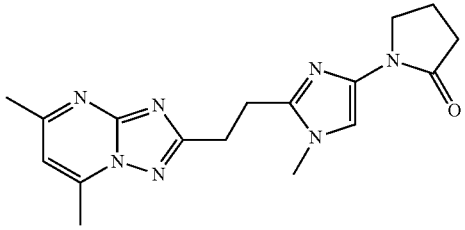 [SMILES: Cc1cc(C)n2nc(CCc3nc(N4CCCC4=O)cn3C)nc2n1]

a: Methyl 5,7-dimethyl-[1,2,4]triazolo[1,5-a]pyrimidine-2-carboxylate

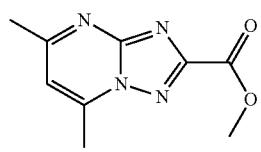

To a stirred solution of 5,7-dimethyl-[1,2,4]triazolo[1,5-a]pyrimidine-2-carboxylic acid (750 mg, 4.05 mmol) at 25° C. in methanol (100 ml) under argon was added H2SO4 (0.05 ml). The mixture was then stirred at 60° C. for 16 h. TLC shows the staring material was complete. The reaction mixture was then cooled and distilled the solvent was removed. After that, water (50 ml) was added to the reaction mixture, and neutral with the sodium bi carbonate. The aqueous phase was extracted with ethyl acetate. The combined organics were washed with brine (50 ml), dried over sodium sulphate, filtered and concentrated to get the crude. The crude was purified by column chromatography via amine silica gel eluted with 40% ethyl acetate in hexane to get methyl 5,7-dimethyl-[1,2,4]triazolo[1,5-a]pyrimidine-2-carboxylate as an off white solid (500 mg, 60%). MS: M/Z=207 (M+H+).

b: {5,7-Dimethyl-[1,2,4]triazolo[1,5-a]pyrimidin-2-yl}methanol

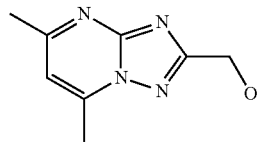

To a stirred solution of Methyl 5,7-dimethyl-[1,2,4]triazolo[1,5-a]pyrimidine-2-carboxylate (300 mg, 1.45 mmol) at 25° C. in methanol (100 ml) under argon, was added sodium borohydride (117 mg, 2.91 mmol) portion wise for 5 min. The mixture was then stirred at 25° C. for 16 h. TLC shows the staring material was complete. After that water (25 ml) was added to the reaction mixture, stirred at 25° C. for 30 min and diluted with DCM (50 ml). The aqueous phase was extracted with 10% methanol in DCM (3×50 ml).

The combined organics were washed with brine (30 ml), dried over sodium sulphate, filtered and concentrated to get the crude which was purified by column chromatography bi amine silica gel eluted with 40% ethyl acetate in hexane to obtained {5,7-dimethyl-[1,2,4]triazolo[1,5-a]pyrimidin-2-yl}methanol (115 mg, 44%) as an off white solid. MS: M/Z=179 (M+H+).

c: 2-(Chloromethyl)-5,7-dimethyl-[1,2,4]triazolo[1, 5-a]pyrimidine

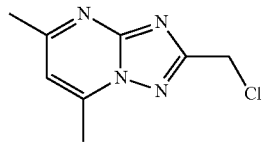

To a stirred solution of {5,7-dimethyl-[1,2,4]triazolo[1,5-a]pyrimidin-2-yl}methanol (200 mg, 02.52 mmol) in dichloromethane (100 ml) under argon at 0° C. was added drop wise Pyridine (0.4 ml, 5.06 mmol) and followed by thionyl chloride (0.25 ml, 3.03 mmol). After then, the mixture was allowed to 25° C. and stirred at 25° C. for 16 h. The reaction mixture was diluted with water (50 ml). The aqueous phase was extracted with ethyl acetate (3×50 ml). The combined organics were washed with brine (30 ml), and sodium bicarbonate solution, dried over sodium sulphate, filtered and concentrated to get the crude. The crude was purified by column chromatography silica gel eluted with 2% methanol in DCM to get 2-(chloromethyl)-5,7-dimethyl-[1,2,4]triazolo[1,5-a]pyrimidine (200 mg, 40%) as an off white solid. MS: M/Z=197 (M+H+).

d: ({5,7-dimethyl-[1,2,4]triazolo[1,5-a]pyrimidin-2-yl}methyl)triphenylphosphanium chloride

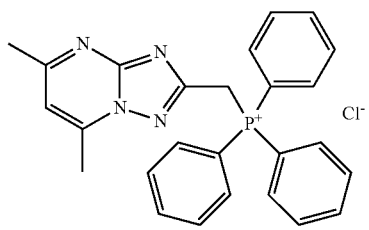 [SMILES: Cc1cc(C)n2nc(C[P+](c3ccccc3)(c3ccccc3)c3ccccc3)nc2n1 ; [Cl-]]

Was prepared in the same manner as described in Example 1a using 2-(chloromethyl)-5,7-dimethyl-[1,2,4]triazolo[1,5-a]pyrimidine (200 mg, 0.102 mmol) as starting material, affording ({5,7-dimethyl-[1,2,4]triazolo[1,5-a]pyrimidin-2-yl}methyl)triphenylphosphanium chloride (270 mg, crude) as yellow solid; MS: M/Z=423 (M+H+).

e: 4-Bromo-2-[(E)-2-{5,7-dimethyl-[1,2,4]triazolo[1,5-a]pyrimidin-2-yl}ethenyl]-1-methyl-1H-imidazole

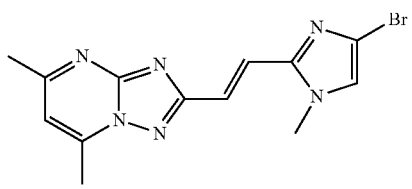 [SMILES: Cc1cc(C)n2nc(/C=C/c3nc(Br)cn3C)nc2n1]

Was prepared in the same manner as described in Example 1c using 4-bromo-1-methyl-1H-imidazole-2-carbaldehyde (150 mg, 0.80 mmol) and ({5,7-dimethyl-[1,2,4]triazolo[1,5-a]pyrimidin-2-yl}methyl)triphenylphosphanium (336 mg, 0.80 mmol) as starting material, affording 4-Bromo-2-[(E)-2-{5,7-dimethyl-[1,2,4]triazolo[1,5-a]pyrimidin-2-yl}ethenyl]-1-methyl-1H-imidazole (75 mg, 28%) as off white solid; MS: M/Z=335 (M+H+).

f: 1-{2-[(E)-2-{5,7-dimethyl-[1,2,4]triazolo[1,5-a]pyrimidin-2-yl}ethenyl]-1-methyl-1H-imidazol-4-yl}pyrrolidin-2-one

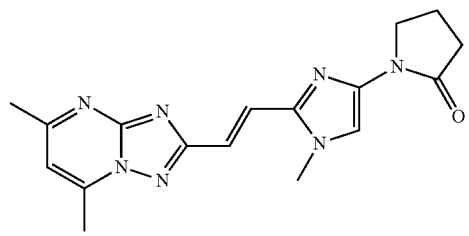 [SMILES: Cc1cc(C)n2nc(/C=C/c3nc(N4CCCC4=O)cn3C)nc2n1]

Was prepared in the same manner as described in Example 10 using 4-bromo-2-[(E)-2-{5,7-dimethyl-[1,2,4]triazolo[1,5-a]pyrimidin-2-yl}ethenyl]-1-methyl-1H-imidazole (60 mg, 0.18 mmol) and pyrrolidin-2-one (0.016 ml, 0.216 mmol) as starting material, affording 1-{2-[(E)-2-{5,7-dimethyl-[1,2,4]triazolo[1,5-a]pyrimidin-2-yl}ethenyl]-1-methyl-1H-imidazol-4-yl}pyrrolidin-2-one (60 mg, crude); MS: M/Z=338.1 (M+H+).

g: 1-[2-(2-{5,7-dimethyl-[1,2,4]triazolo[1,5-a]pyrimidin-2-yl}ethyl)-1-methyl-1H-imidazol-4-yl]pyrrolidin-2-one

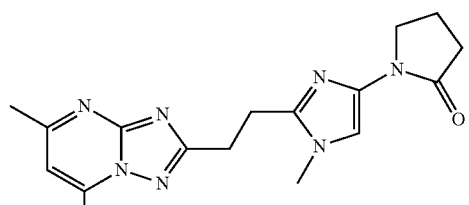

Was prepared in the same manner as described in Example 11 using 41-{2-[(E)-2-{5,7-dimethyl-[1,2,4]triazolo[1,5-a]pyrimidin-2-yl}ethenyl]-1-methyl-1H-imidazol-4-yl}pyrrolidin-2-one (60 mg, 0.18 mmol) as starting material, affording 1-[2-(2-{5,7-dimethyl-[1,2,4]triazolo[1,5-a]pyrimidin-2-yl}ethyl)-1-methyl-1H-imidazol-4-yl]pyrrolidin-2-one (6 mg, 10%) as yellow solid; MS: M/Z=340 (M+H+).

Example 22

1-[2-(2-{5,7-dimethyl-[1,2,4]triazolo[1,5-a]pyrimidin-2-yl}ethyl)-1-methyl-1H-imidazol-4-yl]pyrrolidin-2-one

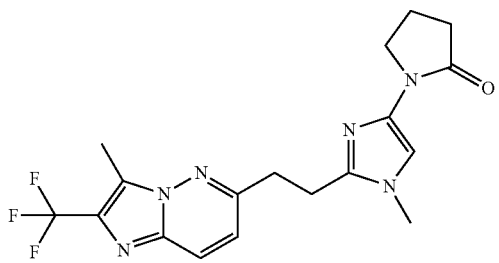

a: 6-Chloropyridazin-3-amine

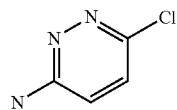

A solution of 3, 6-dichloropyridazine (10.0 g, 67.5 mmol) in 28% aqueous ammonium hydroxide solution (100 ml), taken in a sealed tube, was heated at 120° C. for 17 h. The mixture was cooled to 0° C. precipitate came out. After that resultant precipitate was filtered, and the residue was washed with hexane and dried to give 6-Chloropyridazin-3-amine as white solid (5.0 g, 57%). MS: M/Z=129.9 (M+H+).

b: 6-Chloro-3-methyl-2-(trifluoromethyl) imidazo[1, 2-b]pyridazine

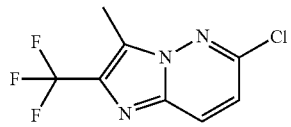

A solution of 6-Chloropyridazin-3-amine (1.0 g, 7.75 mmol) and 3-bromo-1, 1, 1-trifluorobutan-2-one (1.75 g, 37.02 mmol) in dimethoxymethane (10 ml) was heated at 60° C. under argon for 18 h. After completion of reaction cool to 25° C. then volatiles were evaporated off under reduced pressure. Crude residue thus obtained was purified by column chromatography over normal silica gel eluting with 5% EtOAc in hexane to get 6-chloro-3-methyl-2-(trifluoromethyl)imidazo[1,2-b]pyridazine as light brown solid (400 mg, 22%). MS: M/Z=236 (M+H+).

c: 6-Ethenyl-3-methyl-2-(trifluoromethyl) imidazo[1, 2-b]pyridazine

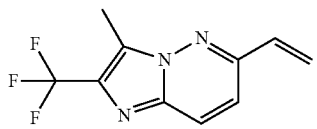 [SMILES: C=Cc1ccc2nc(C(F)(F)F)c(C)n2n1]

A solution of 6-chloro-3-methyl-2-(trifluoromethyl) imidazo[1, 2-b]pyridazine (1.6 g, 6.8 mmol) in DMF (50 ml) in was degassed with argon for 10 min. To this mixture were then added tributyl (vinyl) stannane (2.3 g, 7.48 mmol) and tetrakis (triphenylphosphine) palladium (0) (394 mg, 0.34 mmol) at 25° C. The mixture was again degassed with argon for 10 min and then heated to 80° C. for 5 h. The mixture was cooled to 25° C., diluted with water (100 ml) and aqueous layer was extracted with EtOAc (2×300 ml). Combined organics were washed with ice cold water (3×50 ml) and brine (100 ml), dried over anhydrous Na2SO4, filtered and concentrated in vacuo. Resultant crude mass was purified by column chromatography over normal silica gel eluting with 10% EtOAc in hexane to give 6-ethenyl-3-methyl-2-(trifluoromethyl) imidazo[1, 2-b]pyridazine as yellow solid (1.1 g, 71%). MS: M/Z=228 (M+H+).

d: 3-Methyl-2-(trifluoromethyl) imidazo[1, 2-b]pyridazine-6-carbaldehyde

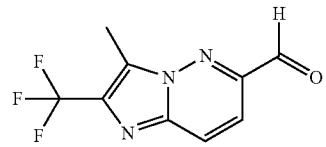 [SMILES: Cc1c(C(F)(F)F)nc2ccc(C=O)nn12]

A solution of 6-ethenyl-3-methyl-2-(trifluoromethyl) imidazo[1, 2-b]pyridazine (1.1 g, 4.86 mmol), osmium tetroxide (4% aq soln, 37 mg, 0.95 ml, 0.14 mmol), sodium periodate (4.14 g, 19.38 mmol) and benzyltriethylammoniumchloride (441 mg, 1.93 mmol) in dioxane (20 ml) and water (4 ml) was heated at 120° C. for 90 minutes. After cooling, solvent was evaporated; the residue was diluted with ethyl acetate (2×200 ml) and washed with (2×150 ml) water and brine. The organic layer was separated, dried over sodium sulfate, filtrated and evaporated to obtain the crude. Resultant crude mass was purified by column chromatography over normal silica gel eluting with 20% EtOAc in hexane to give 3-methyl-2-(trifluoromethyl) imidazo[1, 2-b] pyridazine-6-carbaldehyde (700 mg, 63%) as white solid. MS: M/Z=230 (M+H+).

e: [3-methyl-2-(trifluoromethyl) imidazo[1, 2-b]pyridazin-6-yl]methanol

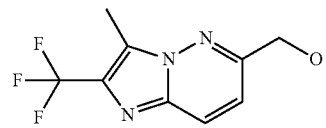 [SMILES: Cc1c(C(F)(F)F)nc2ccc(CO)nn12]

To a solution of 3-methyl-2-(trifluoromethyl) imidazo[1, 2-b]pyridazine-6-carbaldehyde (700 mg, 3.05 mmol) in MeOH (5 ml) and DCM (5 ml) at 25° C. under argon, followed by sodium borohydride (251 mg, 6.11 mmol) in one portion. The mixture was stirred at 25° C. for 2 heater completion of reaction the mixture was quenched with ice water and distilled off the methanol, diluted with DCM (100 ml), and washed with water (50 ml). Aqueous phase was extracted with DCM (2×100 ml). Combined organics were dried over anhydrous Na2SO4, filtered and concentrated in vacuo. Resultant crude material was triturated with hexane and filtered to [3-methyl-2-(trifluoromethyl) imidazo[1, 2-b]pyridazin-6-yl]methanol as pale yellow solid (500 mg, 70%). MS: M/Z=232 (M+H+).

f: 6-(Chloromethyl)-3-methyl-2-(trifluoromethyl) imidazo[1, 2-b]pyridazine

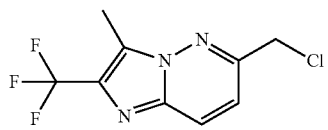 [SMILES: Cc1c(C(F)(F)F)nc2ccc(CCl)nn12]

To a solution of (3-methyl-2-(trifluoromethyl) imidazo[1, 2-b]pyridazin-6-yl]methanol (500 mg, 2.16 mmol) in DCM (10 ml) at 0° C. under nitrogen was added thionyl chloride (0.32 ml, 4.32 mmol) drop wise. The mixture was allowed to stir at 25° C. for 15 min, and then heated to 40° C. for 2 h. After completion of reaction volatiles were removed in vacuo. Resultant crude mass was purified by combiflash column chromatography using 20% ethyl acetate in hexane to give 6-(chloromethyl)-3-methyl-2-(trifluoromethyl) imidazo[1, 2-b]pyridazine as yellow solid (450 mg, 83%). MS: M/Z=250 (M+H+).

g: {[3-Methyl-2-(trifluoromethyl) imidazo[1, 2-b]pyridazin-6-yl]methyl}triphenylphosphanium chloride

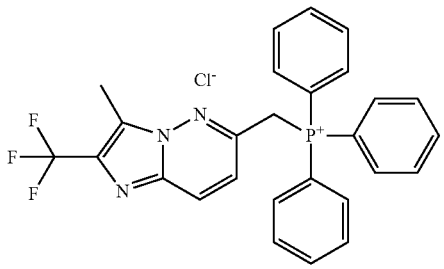 [SMILES: Cc1c(C(F)(F)F)nc2ccc(C[P+](c3ccccc3)(c3ccccc3)c3ccccc3)nn12 ; [Cl-]]

Was prepared in the same manner as described in Example 1a using 6-(chloromethyl)-3-methyl-2-(trifluoromethyl) imidazo[1, 2-b]pyridazine (45 mg, 1.80 mmol) and triphenyl phosphine (521 mg, 1.98 mmol) as starting material, affording {[3-methyl-2-(trifluoromethyl) imidazo[1, 2-b]pyridazin-6-yl]methyl}triphenylphosphanium chloride (800 mg, crude) as grey colored solid.

h: 4-Bromo-1-methyl-2-[(E)-2-[3-methyl-2-(trifluoromethyl) imidazo[1, 2-b]pyridazin-6-yl]ethenyl]-1H-imidazol

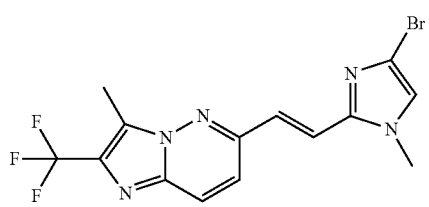 [SMILES: Cc1c(C(F)(F)F)nc2ccc(/C=C/c3nc(Br)cn3C)nn12]

Was prepared in the same manner as described in Example 1c using 4-bromo-1-methyl-1H-imidazole-2-carbaldehyde (200 mg, 1.05 mmol) and {[3-methyl-2-(trifluoromethyl)imidazo[1,2-b]pyridazin-6-yl]methyl}triphenylphosphaniumchloride (504 mg, 1.05 mmol) as starting material, affording 4-bromo-1-methyl-2-[(E)-2-[3-methyl-2-(trifluoromethyl) imidazo[1, 2-b]pyridazin-6-yl]ethenyl]-1H-imidazol (210 mg, 52%) as brown solid. MS: M/Z=386.0 (M+H+).

i: {[3-Methyl-2-(trifluoromethyl) imidazo[1, 2-b]pyridazin-6-yl]methyl}triphenylphosphanium chloride

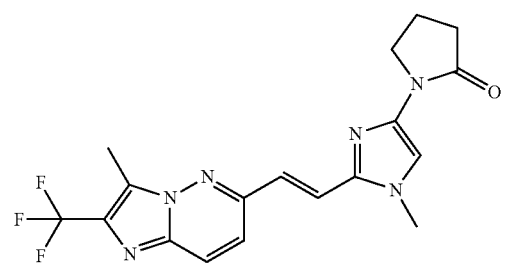 [SMILES: Cc1c(C(F)(F)F)nc2ccc(/C=C/c3nc(N4CCCC4=O)cn3C)nn12]

Was prepared in the same manner as described in Example 10 using 4-bromo-1-methyl-2-[(E)-2-[3-methyl-2-(trifluoromethyl) imidazo[1, 2-b]pyridazin-6-yl]ethenyl]-1H-imidazol (150 mg, 0.39 mmol) and pyrrolidin-2-one (0.06 ml, 0.78 mmol) as starting material, affording 1-{1-methyl-2-[(E)-2-[3-methyl-2-(trifluoromethyl) imidazo[1, 2-b]pyridazin-6-yl]ethenyl]-1H-imidazol-4-yl}pyrrolidin-2-one (80 mg, 52%) as a yellow solid. MS: M/Z=391.0 (M+H+).

j: 1-(1-Methyl-2-{2-[3-methyl-2-(trifluoromethyl) imidazo[1, 2-b]pyridazin-6-yl]ethyl}-1H-imidazol-4yl) pyrrolidin-2-one

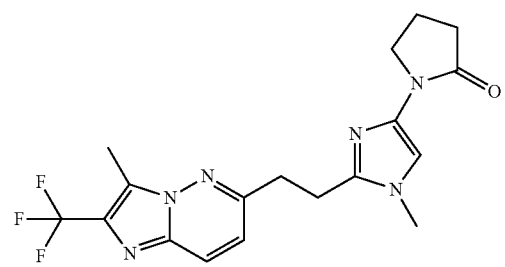 [SMILES: Cc1c(C(F)(F)F)nc2ccc(CCc3nc(N4CCCC4=O)cn3C)nn12]

Was prepared in the same manner as described in Example 11 using 1-{1-methyl-2-[(E)-2-[3-methyl-2-(trifluoromethyl) imidazo[1, 2-b]pyridazin-6-yl]ethenyl]-1H-imidazol-4-yl}pyrrolidin-2-one (80 mg, 0.21 mmol) as starting material, affording 1-(1-Methyl-2-{2-[3-methyl-2-(trifluoromethyl) imidazo[1, 2-b]pyridazin-6-yl]ethyl}-1H-imidazol-4yl) pyrrolidin-2-one (14 mg, 18%) as off white solid. MS: M/Z=393.0 (M+H+).

Example 23

1-(2-{2-[3-Methyl-2-(trifluoromethyl)imidazo[1,2-b]pyridazin-6-yl]ethyl}-1-phenyl-1H-imidazol-4yl)pyrrolidin-2-one

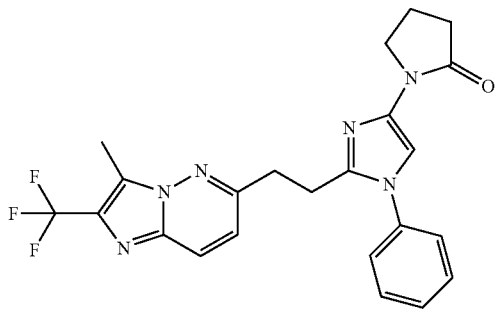 [SMILES: Cc1c(C(F)(F)F)nc2ccc(CCc3nc(N4CCCC4=O)cn3-c3ccccc3)nn12]

a: 4-Bromo-2-[(E)-2-[3-methyl-2-(trifluoromethyl)imidazo[1,2-b]pyridazin-6-yl]ethenyl]-1-phenyl-1H-imidazole

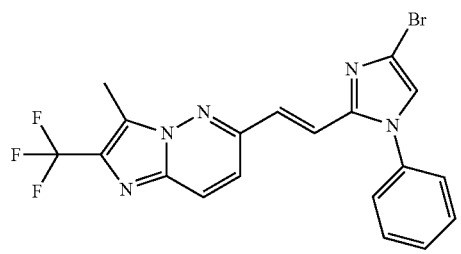 [SMILES: Cc1c(C(F)(F)F)nc2ccc(/C=C/c3nc(Br)cn3-c3ccccc3)nn12]

Was prepared in the same manner as described in Example 1c using 4-bromo-1-phenyl-1H-imidazole-2-carbaldehyde (200 mg, 0.79 mmol) and {[3-methyl-2-(trifluoromethyl)imidazo[1,2-b]pyridazin-6-yl]methyl}triphenylphosphaniumchloride (380 mg, 0.79 mmol) as starting material, affording 4-Bromo-2-[(E)-2-[3-methyl-2-(trifluoromethyl) imidazo[1,2-b]pyridazin-6-yl]ethenyl]-1-phenyl-1H-imidazole (180 mg, 50%) as white solid; MS: M/Z=450 (M+H+).

b: 1-{2-[(E)-2-[3-Methyl-2-(trifluoromethyl)imidazo[1,2-b]pyridazin-6-yl]ethenyl]-1-phenyl-1H-imidazol-4-yl}pyrrolidin-2-one

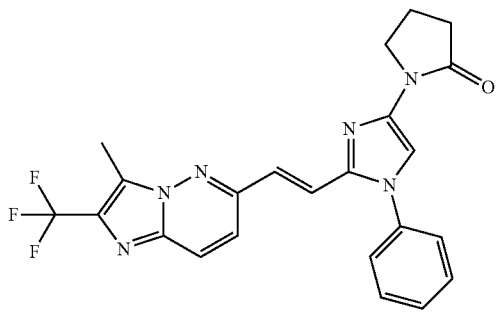 [SMILES: Cc1c(C(F)(F)F)nc2ccc(/C=C/c3nc(N4CCCC4=O)cn3-c3ccccc3)nn12]

Was prepared in the same manner as described in Example 10 using 4-bromo-2-[(E)-2-[3-methyl-2-(trifluoromethyl)imidazo[1,2-b]pyridazin-6-yl]ethenyl]-1-phenyl-1H-imidazole (150 mg, 0.335 mmol) and pyrrolidin-2-one (0.05 ml, 0.67 mmol) as starting material, affording 1-{2-[(E)-2-[3-Methyl-2-(trifluoromethyl)imidazo[1,2-b]pyridazin-6-yl]ethenyl]-1-phenyl-1H-imidazol-4-yl}pyrrolidin-2-one (70 mg, 46%) as yellow solid; MS: M/Z=452 (M+H+).

c: 1-(2-{2-[3-Methyl-2-(trifluoromethyl)imidazo[1,2-b]pyridazin-6-yl]ethyl}-1-phenyl-1H-imidazol-4yl)pyrrolidin-2-one

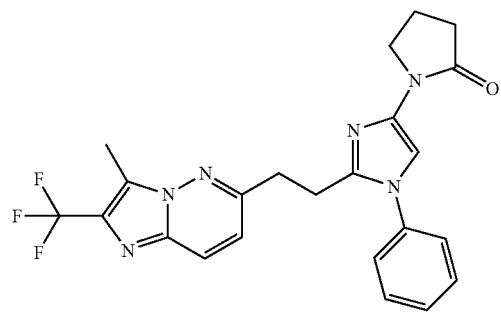 [SMILES: Cc1c(C(F)(F)F)nc2ccc(CCc3nc(N4CCCC4=O)cn3-c3ccccc3)nn12]

Was prepared in the same manner as described in Example 11 using 1-{2-[(E)-2-[3-Methyl-2-(trifluoromethyl)imidazo[1,2-b]pyridazin-6-yl]ethenyl]-1-phenyl-1H-imidazol-4-yl}pyrrolidin-2-one (70 mg, 0.155 mmol) as starting material, affording 1-(2-{2-[3-Methyl-2-(trifluoromethyl)imidazo[1,2-b]pyridazin-6-yl]ethyl}-1-phenyl-1H-imidazol-4yl)pyrrolidin-2-one (12 mg, 17%) as yellow solid; MS: M/Z=455 (M+H+).

Example 24

1-(1-Methyl-2-{2-[3-methyl-2-(trifluoromethyl)imidazo[1,2-b]pyridazin-6-yl]ethynyl}-1H-imidazol-4-yl)pyrrolidin-2-one

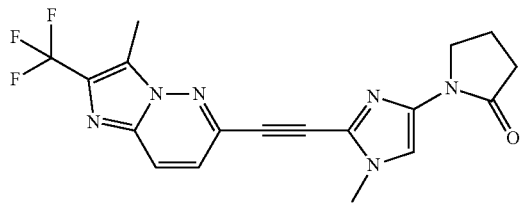 [SMILES: Cc1c(C(F)(F)F)nc2ccc(C#Cc3nc(N4CCCC4=O)cn3C)nn12]

a: 6-Iodopyridazin-3-amine

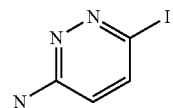

A solution of 6-chloropyridazin-3-amine (2.5 gm, 19.38 mmol) in hydroid acid 57% in water (11.601 ml, 155.04 mmol) was heated up to 100° C. and continued for 18 h. The reaction was cooled to room temperature and ethyl acetate (5 ml) was added. The suspension was vigorously stirred for another 5 minute at 25° C. The solid was collected by filtration, washed with ethyl acetate and dried under vacuum to get yellow solid crystals. The solid was taken up in methanol (60 ml) and sodium hydroxide (0.93 gm, 23.256 mmol) was added. The suspension was heated at 100° C. for 5 min. and cooled to 25° C. again. The reaction mass was concentrated under reduced pressure and washed with water to get pure 6-iodopyridazin-3-amine (2 g, 43%) as white solid. LC-MS (ESI): 222 (M+1).

b: 6-Iodo-3-methyl-2-(trifluoromethyl) imidazo[1, 2-b]pyridazine

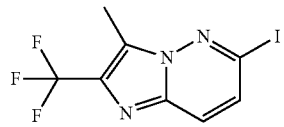

Was prepared in the same manner as described in Example 22b using 6-Iodopyridazin-3-amine (500 mg, 2.26 mmol) and 3-bromo-1, 1, 1-trifluorobutan-2-one (555 mg, 2.7 mmol) as starting material, affording 6-Iodo-3-methyl-2-(trifluoromethyl) imidazo[1, 2-b]pyridazine (200 mg, 27%) as brown sticky solid MS: M/Z=328 (M+H+).

c: 1-(1-Methyl-2-{2-[3-methyl-2-(trifluoromethyl) imidazo[1,2-b]pyridazin-6-yl]ethynyl}-1H-imidazol-4-yl)pyrrolidin-2-one

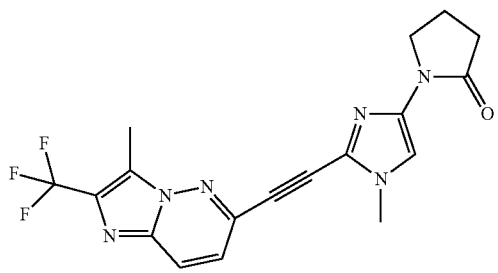 [SMILES: Cc1c(C(F)(F)F)nc2ccc(C#Cc3nc(N4CCCC4=O)cn3C)nn12]

Was prepared in the same manner as described in Example 15c using 1-(2-ethynyl-1-methyl-1H-imidazol-4-yl) pyrrolidin-2-one (30 mg, 0.16 mmol) and 6-iodo-3-methyl-2-(trifluoromethyl) imidazo[1, 2-b]pyridazine (57 mg, 0.17 mmol) as starting material, affording 1-(1-Methyl-2-{2-[3-methyl-2-(trifluoromethyl) imidazo[1, 2-b] pyridazin-6-yl]ethynyl}-1H-imidazol-4-yl) pyrrolidin-2-one (4 mg, 6%) as a yellow solid. MS: M/Z=389 (M+H+).

Example 25

1-(2-{2-[3-methyl-2-(trifluoromethyl) imidazo[1, 2-b]pyridazin-6-yl]ethynyl}-1-phenyl-1H-imidazol-4-yl) pyrrolidin-2-one

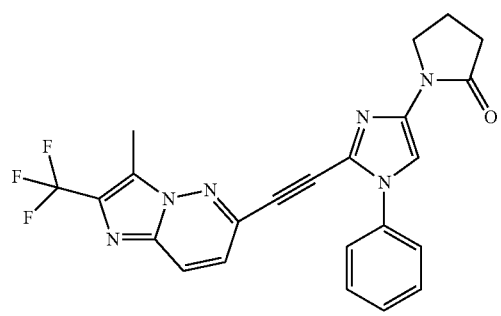 [SMILES: Cc1c(C(F)(F)F)nc2ccc(C#Cc3nc(N4CCCC4=O)cn3-c3ccccc3)nn12]

a: 4-(2-Oxopyrrolidin-1-yl)-1-phenyl-1H-imidazole-2-carbaldehyde

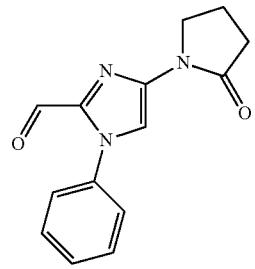 [SMILES: O=Cc1nc(N2CCCC2=O)cn1-c1ccccc1]

Was prepared in the same manner as described in Example 15a using 4-bromo-1-phenyl-1H-imidazole-2-carbaldehyde (800 mg, 3.18 mmol) and pyrrolidin-2-one (0.54 ml, 6.35 mmol) as starting material, affording 4-(2-Oxopyrrolidin-1-yl)-1-phenyl-1H-imidazole-2-carbaldehyde (50 mg, 7%) as white sticky solid; MS: M/Z=256 (M+H+).

b: 1-(2-Ethynyl-1-phenyl-1H-imidazol-4-yl) pyrrolidin-2-one

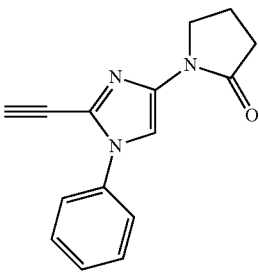 [SMILES: C#Cc1nc(N2CCCC2=O)cn1-c1ccccc1]

Was prepared in the same manner as described in Example 15b using 4-(2-oxopyrrolidin-1-yl)-1-phenyl-1H-imidazole-2-carbaldehyde (90 mg, 0.35 mmol) as starting material, affording 1-(2-Ethynyl-1-phenyl-1H-imidazol-4-yl) pyrrolidin-2-one (18 mg, 20%) as brown sticky solid; MS: M/Z=252.2 (M+H+).

c: 1-(2-{2-[3-methyl-2-(trifluoromethyl) imidazo[1,2-b]pyridazin-6-yl]ethynyl}-1-phenyl-1H-imidazol-4-yl) pyrrolidin-2-one

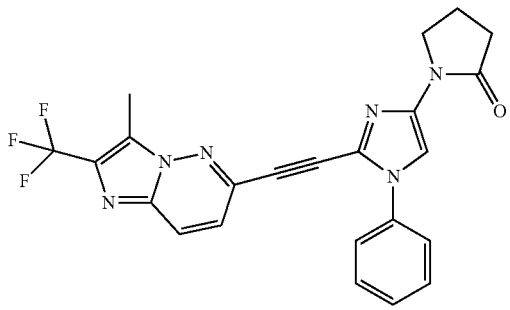 [SMILES: Cc1c(C(F)(F)F)nc2ccc(C#Cc3nc(N4CCCC4=O)cn3-c3ccccc3)nn12]

Was prepared in the same manner as described in Example 15c using 1-(2-ethynyl-1-phenyl-1H-imidazol-4-yl) pyrrolidin-2-one (18 mg, 0.07 mmol) and (6-iodo-3-methyl-2-(trifluoromethyl) imidazo[1, 2-b]pyridazine (26 mg, 0.08 mmol) as starting material, affording 1-(2-{2-[3-methyl-2-(trifluoromethyl) imidazo[1, 2-b]pyridazin-6-yl] ethynyl}-1-phenyl-1H-imidazol-4-yl) pyrrolidin-2-one (5 mg, 15%) as brown sticky solid; MS: M/Z=451 (M+H+).

Example 26

N,3-Dimethyl-6-{2-[1-methyl-4-(2-oxopyrrolidin-1-yl)-1H-imidazol-2-yl]ethyl}-2-trifluoromethyl)imidazo[1,2-b]pyridazine-8-carboxamide

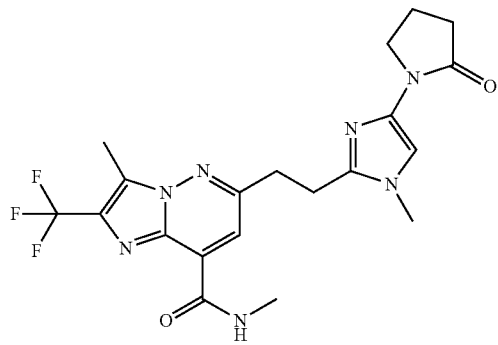 [SMILES: CNC(=O)c1cc(CCc2nc(N3CCCC3=O)cn2C)nn2c(C)c(C(F)(F)F)nc12]

a: 3,6-Dichloropyridazine-4-carbonyl chloride

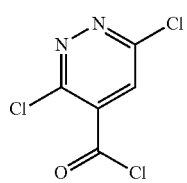 [SMILES: O=C(Cl)c1cc(Cl)nnc1Cl]

To a solution of 3,6-dichloropyridazine-4-carboxylic acid (5 g, 26.04 mmol) in DCM (50 ml) was added oxalyl chloride (2.5 ml, 28.64 mmol) at 0° C. followed by catalytic amount DMF (0.1 ml) under argon. The reaction mass was stirred for 5 h at 25° C. After completion of reaction, solvent was removed under reduced pressure under nitrogen to remove the volatiles and evaporated to give 3, 6-dichloropyridazine-4-carbonyl chloride (5.5 g, crude) as white liquid. This crude was used for the next step.

b: 3,6-Dichloro-N-methylpyridazine-4-carboxamide

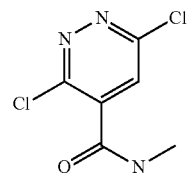

To a solution of 3,6-dichloropyridazine-4-carbonyl chloride (5.5 g, 26.6 mmol) in DCM (50 ml) was added methyl amine (2M in THF, 26 ml) followed by TEA (7.4 ml, 52.13 mmol) at 0° C. under argon. The reaction mass was stirred for 1 h at 25° C. After completion of reaction, reaction mixture diluted with water and extracted with DCM (2×300 ml), the separated organic layers were washed with water (2×100 ml) and brine (100 ml), dried over sodium sulfate, filtered and evaporated to get the crude. The crude was purified by combi-flash chromatography using 20% ethyl acetate in hexane to give 3,6-dichloro-N-methylpyridazine-4-carboxamide (3.2 g, 60%) as white solid.

c: 3-Amino-6-chloro-N-methylpyridazine-4-carb oxamide

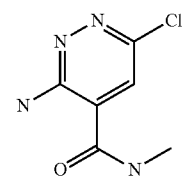

A solution of 3, 6-dichloro-N-methylpyridazine-4-carboxamide (6.6 g, 32.19 mmol) in 28% aqueous ammonium hydroxide solution (100 ml), taken in a sealed tube, was heated at 120° C. for 16 h. The mixture was cooled to 0° C. precipitate came out. After that resultant precipitate was filtered, and the residue was washed with hexane and dried to give 3-amino-6-chloro-N-methylpyridazine-4-carboxamide as white solid (2.2 g, 50%). MS: M/Z=187 (M+H+).

d: 6-Chloro-N,3-dimethyl-2-(trifluoromethyl)imidazo[1,2-b]pyridazine-8-carboxamide

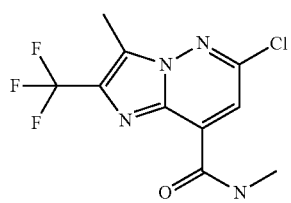 [SMILES: CNC(=O)c1cc(Cl)nn2c(C)c(C(F)(F)F)nc12]

A solution of 3-amino-6-chloro-N-methylpyridazine-4-carboxamide (6.7 g, 36.02 mmol) and 3-bromo-1, 1, 1-trifluorobutan-2-one (4.3 ml, 36.02 mmol) in dimethoxymethane (100 ml) was heated at 60° C. under argon for 18 h. After completion of reaction cooled to 25° C. then volatiles were evaporated off under reduced pressure. Crude residue thus obtained was purified column chromatography over normal silica gel eluting with 5% EtOAc in hexane to get 6-chloro-N,3-dimethyl-2-(trifluoromethyl)imidazo[1,2-b]pyridazine-8-carboxamide as off white solid (3 g, 28%). MS: M/Z=293 (M+H+).

e: 6-Ethenyl-N,3-dimethyl-2-(trifluoromethyl)imidazo[1,2-b]pyridazine-8-carboxamide

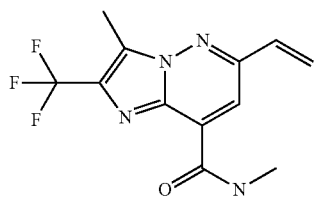 [SMILES: C=Cc1cc(C(=O)NC)c2nc(C(F)(F)F)c(C)n2n1]

A solution of 6-chloro-N, 3-dimethyl-2-(trifluoromethyl) imidazo[1, 2-b]pyridazine-8-carboxamide (3 g, 10.27 mmol) in DMF (10 ml) in was degassed with argon for 10 min. To this mixture were then added tributyl (vinyl) stannane (3.9 g, 12.32 mmol) and tetrakis (triphenylphosphine) palladium (0) (594 mg, 0.514 mmol) at 25° C. The mixture was again degassed with argon for 10 min and then heated to 80° C. for 5 h. The mixture was cooled to 25° C., diluted with water (100 ml) and aqueous layer was extracted with EtOAc (2×300 ml). Combined organics were washed with ice cold water (3×50 ml) and brine (100 ml), dried over anhydrous Na2SO4, filtered and concentrated in vacuo. Resultant crude mass was purified by column chromatography over normal silica gel eluting with 10% EtOAc in hexane to give 6-ethenyl-N,3-dimethyl-2-(trifluoromethyl) imidazo[1,2-b]pyridazine-8-carboxamide as off white solid (1.1 g, 38%). MS: M/Z=285 (M+H+).

f: 6-Formyl-N,3-dimethyl-2-(trifluoromethyl)imidazo[1,2-b]pyridazine-8-carb oxamide

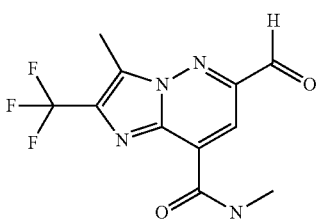 [SMILES: CNC(=O)c1cc(C=O)nn2c(C)c(C(F)(F)F)nc12]

A solution of 6-ethenyl-N,3-dimethyl-2-(trifluoromethyl) imidazo[1,2-b]pyridazine-8-carboxamide (1.1 g, 3.87 mmol), osmium tetroxide (4% aq soln, 30 mg, 0.90 ml, 0.12 mmol), sodium periodate (3.3 g, 15.4 mmol) and benzyltriethylammoniumchloride (370 mg, 1.63 mmol) in dioxane (44 ml) and water (11 ml) was heated at 120° C. for 5 h. After cooling, solvent was evaporated; the residue was diluted with ethyl acetate (2×200 ml) and washed with (2×150 ml) water and brine. The organic layer was separated, dried over sodium sulfate, filtrated and evaporated to obtain the crude. Resultant crude mass was purified by column chromatography over normal silica gel eluting with 20% EtOAc in hexane to give 6-formyl-N,3-dimethyl-2-(trifluoromethyl)imidazo[1,2-b]pyridazine-8-carboxamide (800 mg, crude) as Light yellow solid. MS: M/Z=286 (M+H+).

g: 6-(Hydroxymethyl)-N,3-dimethyl-2-(trifluoromethyl)imidazo[1,2-b]pyridazine-8-carboxamide

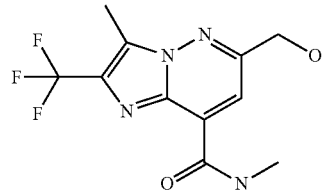 [SMILES: CNC(=O)c1cc(CO)nn2c(C)c(C(F)(F)F)nc12]

Was prepared in the same manner as described in Example 22e using 6-formyl-N,3-dimethyl-2-(trifluoromethyl)imidazo[1,2-b]pyridazine-8-carboxamide (800 mg, 2.79 mmol) as starting material, affording 6-(Hydroxymethyl)-N,3-dimethyl-2-(trifluoromethyl)imidazo[1,2-b]pyridazine-8-carboxamide (240 mg, 30%). MS: M/Z=289 (M+H+).

h: 6-(Chloromethyl)-N,3-dimethyl-2-(trifluoromethyl)imidazo[1,2-b]pyridazine-8-carboxamide

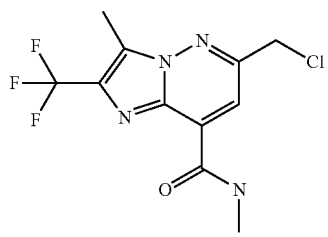 [SMILES: CNC(=O)c1cc(CCl)nn2c(C)c(C(F)(F)F)nc12]

Was prepared in the same manner as described in Example 22f using 6-(hydroxymethyl)-N,3-dimethyl-2-(trifluoromethyl)imidazo[1,2-b]pyridazine-8-carboxamide (240 mg, 0.84 mmol) as starting material, affording 6-(Chloromethyl)-N,3-dimethyl-2-(trifluoromethyl)imidazo[1,2-b]pyridazine-8-carboxamide (150 mg, 59%) as off white solid. MS: M/Z=307 (M+H+).

i: {[3-methyl-8-(methylcarbamoyl)-2-(trifluoromethyl) imidazo[1, 2-b]pyridazin-6-yl]methyl}triphenylphosphanium chloride

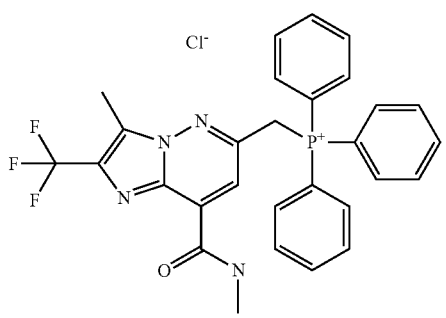 [SMILES: CNC(=O)c1cc(C[P+](c2ccccc2)(c2ccccc2)c2ccccc2)nn2c(C)c(C(F)(F)F)nc12 ; [Cl-]]

63

Was prepared in the same manner as described in Example 1a using 6-(chloromethyl)-N, 3-dimethyl-2-(trifluoromethyl) imidazo[1, 2-b]pyridazine-8-carboxamide (150 mg, 0.50 mmol) and triphenyl phosphine (192 mg, 0.58 mmol) as starting material, affording {[3-methyl-8-(methylcarbamoyl)-2-(trifluoromethyl) imidazo[1, 2-b]pyridazin-6-yl]methyl}triphenylphosphanium chloride (320 mg, crude) as off white solid. MS: M/Z=533 (M+H+).

j: 6-[(E)-2-(4-Bromo-1-methyl-1H-imidazol-2-yl)ethenyl]-N, 3-dimethyl-2-(trifluoromethyl) imidazo[1, 2-b]pyridazine-8-carboxamide

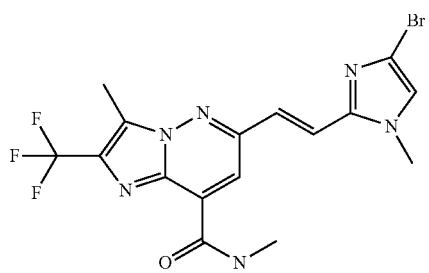 [SMILES: CNC(=O)c1cc(/C=C/c2nc(Br)cn2C)nn2c(C)c(C(F)(F)F)nc12]

Was prepared in the same manner as described in Example 5a using 4-bromo-1-methyl-1H-imidazole-2-carbaldehyde (85 mg, 0.45 mmol) and {[3-methyl-8-(methylcarbamoyl)-2-(trifluoromethyl)imidazo[1,2-b]pyridazin-6-yl]methyl}triphenylphosphaniumchloride (240 mg, 0.45 mmol) as starting material, affording 6-[(E)-2-(4-Bromo-1-methyl-1H-imidazol-2-yl) ethenyl]-N, 3-dimethyl-2-(trifluoromethyl) imidazo[1, 2-b]pyridazine-8-carboxamide) (90 mg, 45%) as yellow solid. MS: M/Z=445.0 (M+H+).

k: N,3-Dimethyl-6-[(E)-2-[1-methyl-4-(2-oxopyrrolidin-1-yl)-1H-imidazol-2-yl]ethenyl]-2-(trifluoromethyl) imidazo[1,2-b]pyridazine-8-carboxamide

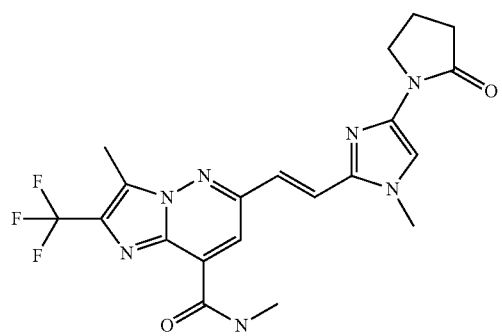 [SMILES: CNC(=O)c1cc(/C=C/c2nc(N3CCCC3=O)cn2C)nn2c(C)c(C(F)(F)F)nc12]

Was prepared in the same manner as described in Example 10 using 6-[(E)-2-(4-bromo-1-methyl-1H-imidazol-2-yl)ethenyl]-N,3-dimethyl-2-(trifluoromethyl) imidazo[1,2-b]pyridazine-8-carboxamide (60 mg, 0.14 mmol) as starting material, affording N,3-Dimethyl-6-[(E)-2-[1-methyl-4-(2-oxopyrrolidin-1-yl)-1H-imidazol-2-yl]ethenyl]-2-(trifluoromethyl) imidazo[1,2-b]pyridazine-8-carboxamide (20 mg, 33%) as a white solid. MS: M/Z=448.0 (M+H+).

64 l: N,3-Dimethyl-6-{2-[1-methyl-4-(2-oxopyrrolidin-1-yl)-1H-imidazol-2-yl]ethyl}-2-trifluoromethyl)imidazo[1,2-b]pyridazine-8-carboxamide

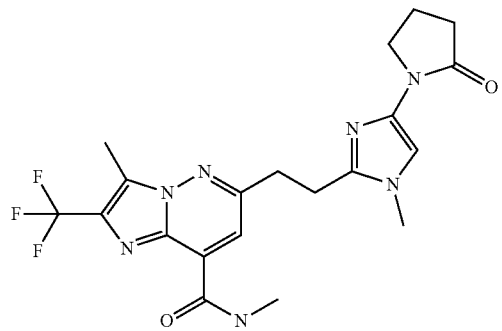 [SMILES: CNC(=O)c1cc(CCc2nc(N3CCCC3=O)cn2C)nn2c(C)c(C(F)(F)F)nc12]

Was prepared in the same manner as described in Example 11 using N,3-dimethyl-6-[(E)-2-[1-methyl-4-(2-oxopyrrolidin-1-yl)-1H-imidazol-2-yl]ethenyl]-2-(trifluoromethyl) imidazo[1,2-b]pyridazine-8-carboxamide (20 mg, 0.05 mmol) as starting material, affording N,3-Dimethyl-6-{2-[1-methyl-4-(2-oxopyrrolidin-1-yl)-1H-imidazol-2-yl]ethyl}-2-trifluoromethyl)imidazo[1,2-b]pyridazine-8-carboxamide (14 mg, 69%) as off white solid. MS: M/Z=450.0 (M+H+).

Example 27

N,3-Dimethyl-6-{2-[4-(2-oxopyrrolidin-1-yl)-1-phenyl-1H-imidazol-2-yl]ethyl}-2-(trifluoromethyl)imidazo[1,2-b]pyridazine-8-carb oxamide

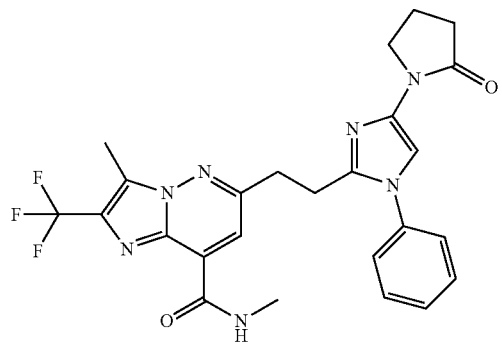 [SMILES: CNC(=O)c1cc(CCc2nc(N3CCCC3=O)cn2-c2ccccc2)nn2c(C)c(C(F)(F)F)nc12]

a: 6-[(E)-2-(4-Bromo-1-phenyl-1H-imidazol-2-yl)ethenyl]-N, 3-dimethyl-2-(trifluoromethyl) imidazo[1, 2-b]pyridazine-8-carboxamide

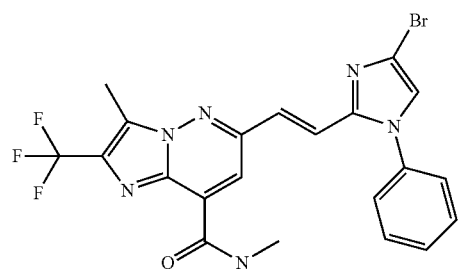 [SMILES: CNC(=O)c1cc(/C=C/c2nc(Br)cn2-c2ccccc2)nn2c(C)c(C(F)(F)F)nc12]

Was prepared in the same manner as described in Example 5a using 4-bromo-1-phenyl-1H-imidazole-2-carbaldehyde (150 mg, 0.6 mmol) and {[3-methyl-8-(methylcarbamoyl)-2-(trifluoromethyl)imidazo[1,2-b]pyridazin-6-yl]methyl}triphenyl phosphaniumchloride (318 mg, 0.6 mmol) as starting material, affording 6-[(E)-2-(4-Bromo-1-phenyl-1H-imidazol-2-yl) ethenyl]-N, 3-dimethyl-2-(trifluoromethyl) imidazo[1, 2-b]pyridazine-8-carboxamide (150 mg, crude) as white solid; MS: M/Z=506 (M+H+).

b: N,3-Dimethyl-6-[(E)-2-[4-(2-oxopyrrolidin-1-yl)-1-phenyl-1H-imidazol-2-yl]ethenyl]-2-(trifluoromethyl) imidazo[1,2-b]pyridazine-8-carboxamide

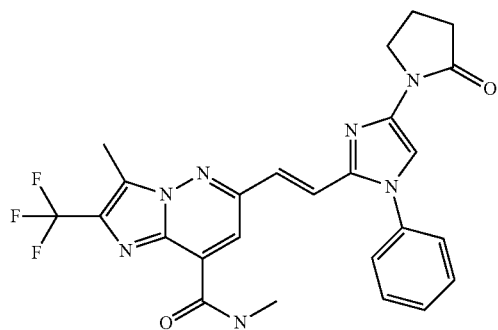 [SMILES: CNC(=O)c1cc(/C=C/c2nc(N3CCCC3=O)cn2-c2ccccc2)nn2c(C)c(C(F)(F)F)nc12]

Was prepared in the same manner as described in Example 10 using 6-[(E)-2-(4-bromo-1-phenyl-1H-imidazol-2-yl)ethenyl]-N,3-dimethyl-2-(trifluoromethyl) imidazo[1,2-b]pyridazine-8-carboxamide (110 mg, 0.22 mmol) and pyrrolidin-2-one (0.04 ml, 0.44 mmol) as starting material, affording N,3-Dimethyl-6-[(E)-2-[4-(2-oxopyrrolidin-1-yl)-1-phenyl-1H-imidazol-2-yl]ethenyl]-2-(trifluoromethyl) imidazo[1,2-b]pyridazine-8-carboxamide (70 mg, crude) as off white solid; MS: M/Z=510 (M+H+).

c: N,3-Dimethyl-6-{2-[4-(2-oxopyrrolidin-1-yl)-1-phenyl-1H-imidazol-2-yl]ethyl}-2-(trifluoromethyl) imidazo[1,2-b]pyridazine-8-carboxamide

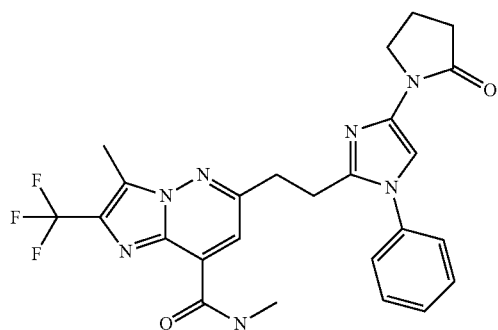 [SMILES: CNC(=O)c1cc(CCc2nc(N3CCCC3=O)cn2-c2ccccc2)nn2c(C)c(C(F)(F)F)nc12]

Was prepared in the same manner as described in Example 11 using N,3-dimethyl-6-[(E)-2-[4-(2-oxopyrrolidin-1-yl)-1-phenyl-1H-imidazol-2-yl]ethenyl]-2-(trifluoromethyl) imidazo[1,2-b]pyridazine-8-carboxamide (70 mg, 0.14 mmol) as starting material, affording N,3-Dimethyl-6-{2-[4-(2-oxopyrrolidin-1-yl)-1-phenyl-1H-imidazol-2-yl]ethyl}-2-(trifluoromethyl)imidazo[1,2-b]pyridazine-8-carboxamide (12 mg, 17%) as yellow solid; MS: M/Z=512 (M+H+).

I claim:
1. A compound of formula (I)

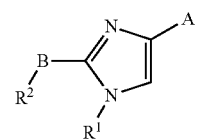

wherein
A is

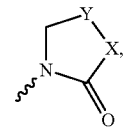

B is $C_1$-$C_4$-alkylene, $C_2$-$C_4$-alkenylene, or $C_2$-$C_4$-alkynylene, $R^1$ is selected from hydrogen, $C_1$-$C_7$-alkyl, $C_1$-$C_7$-alkoxyalkyl, $C_1$-$C_7$-haloalkyl, —$(CH_2)_{0,1,2}$—$C_3$-$C_5$-cycloalkyl, or —$(CH_2)_{0,1,2}$-(hetero-)aryl optionally substituted by halogen, $C_1$-$C_7$-alkyl or $C_1$-$C_7$ alkoxy, $R^2$ is selected from (i) heteroaryl optionally independently substituted by 1 to 3 substituents selected from halogen, hydroxyl, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—$R^6$—C(O)—$R^7$, heteroaryl, heterocycloalkyl, —$SO_2R^{12}$, —C(O)NR'R", NR'R", wherein R' and R" are independently hydrogen or $C_1$-$C_7$-alkyl, or R' and R" together with the nitrogen atom to which they are attached form a heterocycloalkyl, or (ii) $R^2$ is $C_1$-$C_2$-alkoxy optionally substituted by halogen, $R^6$ and $R^{12}$ are independently $C_1$-$C_7$-alkyl,
$R^7$ is heterocycloalkyl,
X is $NR^3$ or $CR^3$,
Y is $(CH_2)_n$,
n is 1, 2, 3 or 4,
$R^3$ is hydrogen or $C_1$-$C_7$-alkyl.

2. The compound of claim 1, wherein $R^2$ is selected from the group consisting of:

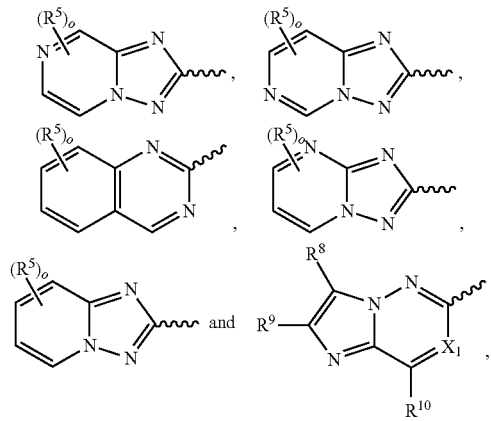

wherein R⁵ in each occurrence is independently selected from hydrogen, halogen, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—R⁶—C(O)—R⁷, —SO₂R¹² or $C_1$-$C_2$-alkoxy optionally substituted by halogen, $C_1$-$C_2$-alkoxy or heterocycloalkyl, o is 0, 1, 2 or 3, R⁸ and R⁹ are independently selected from hydrogen, halogen, $C_1$-$C_7$-alkyl, $C_1$-$C_7$-haloalkyl, $C_1$-$C_7$-hydroxyalkyl, or cyano, or R⁸ and R⁹ together form a $C_3$-$C_8$ cycloalkyl;

R¹⁰ is selected from hydrogen, $C_1$-$C_7$-haloalkoxy, $C_3$-$C_8$ cycloalkyl, $C_1$-$C_7$ alkoxy, hydroxyl, halogen, $S(O)_2$—$C_1$-$C_7$-alkyl, —C(O)NR'R" or NR'R", wherein R' and R" are independently selected from hydrogen or $C_1$-$C_7$-alkyl or R' and R" together with the nitrogen atom to which they are attached from a heterocycloalkyl, or R¹⁰ and R⁴ together form a $C_3$-$C_8$ cycloalkyl, R¹¹ is heteroaryl or heterocycloalkyl X₁ is N or C—R⁴ wherein R⁴ is selected from hydrogen, $C_1$-$C_7$-alkyl, $C_1$-$C_7$ alkoxy, $C_1$-$C_7$-haloalkyl, $C_3$-$C_8$ cycloalkyl or —C(O)NR'R" wherein R' and R" are independently selected from hydrogen or $C_1$-$C_7$-alkyl.

3. The compound of claim 1 wherein R² is selected from the group consisting of:

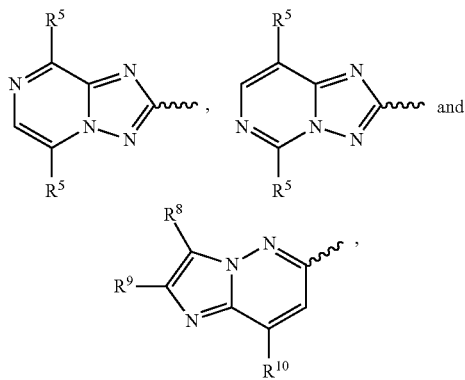

wherein R⁵ in each occurrence is independently selected from hydrogen, halogen, $C_{1-7}$ alkyl or $C_1$-$C_7$-haloalkyl, R⁸ and R⁹ are independently selected from $C_{1-7}$ alkyl or $C_1$-$C_7$-haloalkyl and R¹⁰ is selected from hydrogen or —C(O)NR'R", wherein R' and R" are independently selected from hydrogen or $C_1$-$C_7$-alkyl.

4. The compound of claim 1, wherein B is selected from ethylene, ethenylene or ethynylene.

5. The compound of claim 2, wherein X is CR³, Y is CH₂ and R³ is hydrogen.

6. The compound of claim 2, wherein X is NR³, Y is CH₂ and R³ is $C_{1-7}$ alkyl.

7. The compound of claim 5, wherein R¹ is selected from $C_1$-$C_7$-alkyl, $C_1$-$C_7$-haloalkyl, —(CH₂)$_{0,1,2}$—$C_3$-$C_5$-cycloalkyl or phenyl.

8. The compound of claim 6, wherein R¹ is selected from $C_1$-$C_7$-alkyl, $C_1$-$C_7$-haloalkyl, —(CH₂)$_{0,1,2}$—$C_3$-$C_5$-cycloalkyl or phenyl.

9. The compound of claim 1 selected from the group consisting of:

1-(2-(2-(5,8-dimethyl-[1,2,4]triazolo[1,5-c]pyrimidin-2-yl)ethyl)-1-methyl-1H-imidazol-4-yl)pyrrolidin-2-one;
1-(2-(2-(5,8-dimethyl-[1,2,4]triazolo[1,5-a]pyrazin-2-yl)ethyl)-1-phenyl-1H-imidazol-4-yl)pyrrolidin-2-one;
1-[2-[(E)-2-(5,8-dimethyl-[1,2,4]triazolo[1,5-a]pyrazin-2-yl)ethenyl]-1-phenylimidazol-4-yl]pyrrolidin-2-one;
1-[1-cyclopropyl-2-[(E)-2-(5,8-dimethyl-[1,2,4]triazolo[1,5-a]pyrazin-2-yl)ethenyl]imidazol-4-yl]pyrrolidin-2-one;
1-(1-cyclopropyl-2-(2-(5,8-dimethyl-[1,2,4]triazolo[1,5-a]pyrazin-2-yl)ethyl)-1H-imidazol-4-yl)pyrrolidin-2-one;
1-[2-[(E)-2-(5,8-dimethyl-[1,2,4]triazolo[1,5-a]pyrazin-2-yl)vinyl]-1-methyl-imidazol-4-yl]-3-methyl-imidazolidin-2-one;
1-(2-((4,8-dimethylquinazolin-2-yl)ethynyl)-1-methyl-1H-imidazol-4-yl)pyrrolidin-2-one;
1-{2-[(E)-2-{4,7-dimethyl-[1,2,4]triazolo[1,5-a]pyrazin-2-yl}ethenyl]-1-methyl-1H-imidazol-4-yl}pyrrolidin-2-one;
1-[2-(2-{4,7-Dimethyl-[1,2,4]triazolo[1,5-a]pyrazin-2-yl}ethyl)-1-methyl-1H-imidazol-4-yl]pyrrolidin-2-one;
1-[1-(Cyclopropylmethyl)-2-(2-{4,7-dimethyl-[1,2,4]triazolo[1,5-a]pyrazin-2-yl}ethyl)-1H-imidazol-4-yl]pyrrolidin-2-one;
1-[2-(2-{4,7-Dimethyl-[1,2,4]triazolo[1,5-a]pyrazin-2-yl}ethyl)-1-(2,2,2-trifluoroethyl)-1H-imidazol-4-yl]pyrrolidin-2-one;
1-[1-(2,2-difluoroethyl)-2-(2-{4,7-dimethyl-[1,2,4]triazolo[1,5-a]pyrazin-2-yl}ethyl)-1H-imidazol-4-yl]pyrrolidin-2-one;
1-[2-(2-{4,7-Dimethyl-[1,2,4]triazolo[1,5-a]pyrazin-2-yl}ethynyl)-1-methyl-1H-imidazol-4-yl]pyrrolidin-2-one;
1-[1-(Cyclopropylmethyl)-2-(2-{5,8-dimethyl-[1,2,4]triazolo[1,5-c]pyrimidin-2-yl}ethyl)-1H-imidazol-4-yl]pyrrolidin-2-one;
1-[2-[2-(5,8-dimethyl-[1,2,4]triazolo[1,5-c]pyrimidin-2-yl)ethyl]-1-phenyl-imidazol-4-yl]pyrrolidin-2-one;
1-[2-(2-{5,8-Dimethyl-[1,2,4]triazolo[1,5-c]pyrimidin-2-yl}ethyl)-1-(2,2,2-trifluoroethyl)-1H-imidazol-4-yl]pyrrolidin-2-one;
1-[1-(2,2-difluoroethyl)-2-(2-{5,8-dimethyl-[1,2,4]triazolo[1,5-c]pyrimidin-2-yl}ethyl)-1H-imidazol-4-yl]pyrrolidin-2-one;
1-{2-[(E)-2-{4,7-Dimethyl-[1,2,4]triazolo[1,5-a]pyrazin-2-yl}ethenyl]-1-phenyl-1H-imidazol-4-yl}pyrrolidin-2-one;
1-[2-(2-{5,7-dimethyl-[1,2,4]triazolo[1,5-a]pyrimidin-2-yl}ethyl)-1-methyl-1H-imidazol-4-yl]pyrrolidin-2-one;
1-(2-{2-[3-Methyl-2-(trifluoromethyl)imidazo[1,2-b]pyridazin-6-yl]ethyl}-1-phenyl-1H-imidazol-4-yl)pyrrolidin-2-one;
1-(1-Methyl-2-{2-[3-methyl-2-(trifluoromethyl) imidazo[1,2-b]pyridazin-6-yl]ethynyl}-1H-imidazol-4-yl)pyrrolidin-2-one;
1-(2-{2-[3-methyl-2-(trifluoromethyl) imidazo[1, 2-b]pyridazin-6-yl]ethynyl}-1-phenyl-1H-imidazol-4-yl) pyrrolidin-2-one;
N,3-Dimethyl-6-{2-[1-methyl-4-(2-oxopyrrolidin-1-yl)-1H-imidazol-2-yl]ethyl}-2-(trifluoromethyl)imidazo[1,2-b]pyridazine-8-carboxamide; and,
N,3-Dimethyl-6-{2-[4-(2-oxopyrrolidin-1-yl)-1-phenyl-1H-imidazol-2-yl]ethyl}-2-(trifluoromethyl)imidazo[1,2-b]pyridazine-8-carboxamide.

10. A process for the manufacture of a compound of formula (Ia),

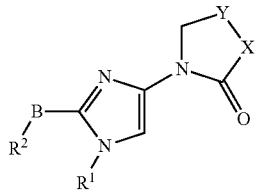

(Ia)

11. A process for the manufacture of a compound of formula (Ib),

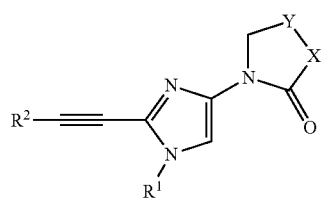

(Ib)

$R^1$ is selected from hydrogen, $C_1$-$C_7$-alkyl, $C_1$-$C_7$-alkoxyalkyl, $C_1$-$C_7$-haloalkyl, —$(CH_2)_{0,1,2}$—$C_3$-$C_5$-cycloalkyl, or —$(CH_2)_{0,1,2}$-(hetero-)aryl optionally substituted by halogen, $C_1$-$C_7$-alkyl or $C_1$-$C_7$ alkoxy, $R^2$ is selected from (i) heteroaryl optionally substituted by 1 to 3 substituents selected from halogen, hydroxyl, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—$R^6$—C(O)—$R^7$, heteroaryl, heterocycloalkyl, —$SO_2R^{12}$, —C(O)NR'R", NR'R" wherein R' and R" are independently hydrogen or $C_1$-$C_7$-alkyl or R' and R" together with the nitrogen atom to which they are attached from a heterocycloalkyl or (ii) $R^2$ is $C_1$-$C_2$-alkoxy optionally substituted by halogen, $R^6$ and $R^{12}$ are independently $C_1$-$C_7$-alkyl, $R^7$ is heterocycloalkyl, X is $NR^3$ or $CR^3$, Y is $(CH_2)_n$, n is 1, 2, 3, 4, $R^3$ is hydrogen or $C_1$-$C_7$-alkyl, a) reacting a compound of formula V,

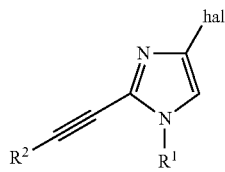

b) with a compound of formula III,

B is $C_1$-$C_4$-alkylene or $C_2$-$C_4$-alkenylene, $R^1$ is selected from hydrogen, $C_1$-$C_7$-alkyl, $C_1$-$C_7$-alkoxyalkyl, $C_1$-$C_7$-haloalkyl, —$(CH_2)_{0,1,2}$—$C_3$-$C_5$-cycloalkyl, —$(CH_2)_{0,1,2}$-(hetero-)aryl optionally substituted by halogen, $C_1$-$C_7$-alkyl or $C_1$-$C_7$ alkoxy, $R^2$ is selected from heteroaryl optionally substituted by 1 to 3 substituents selected from halogen, hydroxyl, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—$R^6$—C(O)—$R^7$, heteroaryl, heterocycloalkyl, —$SO_2R^{12}$, —C(O)NR'R", NR'R" wherein R' and R" are independently hydrogen, $C_1$-$C_7$-alkyl, or R' and R" together with the nitrogen atom to which they are attached from a heterocycloalkyl or (ii) $R^2$ is $C_1$-$C_2$-alkoxy optionally substituted by halogen, $R^6$ and $R^{12}$ are independently $C_1$-$C_7$-alkyl, $R^7$ is heterocycloalkyl, X is $NR^3$ or $CR^3$, Y is $(CH_2)_n$, n is 1, 2, 3, 4, $R^3$ is hydrogen or $C_1$-$C_7$-alkyl, a) reacting a compound of formula II,

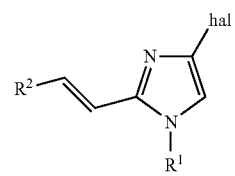

b) with a compound of formula III,

(III)

to afford a compound of formula Ia wherein B is ethenylene which compound can be optionally hydrogenated to afford a compound of formula Ia wherein B is ethylene,

(III)

to afford a compound of formula Ib wherein $R^1$, $R^2$, X and Y are as defined hereinbefore.

12. A method for the treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder which method comprises administering to a patient in need thereof, a therapeutically effective amount of a compound according to claim 1.

13. A pharmaceutical composition comprising a compound of claim 1 and at least one a therapeutically inert excipient, carrier or diluent.

14. The compound according to claim 2 wherein $R^{11}$ a 5- or 6-membered heteroaryl or a 5- or 6-membered heterocycloalkyl.

* * * * *